United States Patent [19]

Skidmore et al.

[11] Patent Number: 4,730,008
[45] Date of Patent: Mar. 8, 1988

[54] AMINOPHENOL DERIVATIVES

[75] Inventors: Ian F. Skidmore, Welwyn; Harry Finch, Hitchin; Alan Naylor, Royston; Lawrence H. C. Lunts, Broxbourne; Ian B. Campbell, Ware, all of England

[73] Assignee: Glaxo Group Limited, London, England

[21] Appl. No.: 817,676

[22] Filed: Jan. 10, 1986

Related U.S. Application Data

[63] Continuation-in-part of Ser. No. 788,120, Oct. 16, 1985, abandoned.

[30] Foreign Application Priority Data

Oct. 17, 1984 [GB] United Kingdom ................ 8426200

[51] Int. Cl.$^4$ .................... C07C 143/74; A61K 31/18
[52] U.S. Cl. .................... 514/605; 514/222; 514/228; 514/229; 514/232; 514/234; 514/235; 514/255; 514/330; 514/331; 514/423; 514/428; 514/456; 514/466; 514/487; 514/484; 514/522; 514/523; 514/524; 514/539; 514/562; 514/563; 514/564; 514/565; 514/597; 514/595; 514/600; 514/629; 544/59; 544/159; 544/165; 544/398; 544/400; 546/226; 546/232; 546/233; 548/567; 548/569; 549/365; 549/441; 549/443; 549/444; 558/408; 558/413; 558/414; 558/422; 560/13; 560/27; 560/34; 560/42; 562/430; 562/439; 562/452; 564/49; 564/50; 564/51; 564/56; 564/79; 564/99; 564/220

[58] Field of Search ...................... 560/13, 29, 42, 27, 560/34; 544/59, 159, 165, 398, 400; 546/232, 226, 233; 548/566, 567; 549/441, 443, 365, 444; 564/49, 51, 79, 99, 223, 220, 50, 56, 221; 514/222, 232, 229, 234, 228, 237, 235, 330, 255, 331, 423, 456, 428, 487, 466, 484, 523, 538, 522, 524, 564, 597, 539, 562, 600, 601, 563, 565, 630, 605, 595, 629; 558/408, 413, 414, 422; 562/430, 439, 452

[56] References Cited

U.S. PATENT DOCUMENTS

| 3,337,546 | 8/1967 | Malatestinic | 564/220 |
| 3,644,520 | 2/1972 | Hartley | 564/220 |
| 4,021,485 | 5/1977 | Schromm | 564/220 |
| 4,146,638 | 3/1979 | Renth | 564/220 |
| 4,396,627 | 8/1983 | Ainsworth | 564/220 |

FOREIGN PATENT DOCUMENTS

| 3524990 | 1/1986 | Fed. Rep. of Germany . |
| 4290M | 8/1967 | France . |
| 9400 | 10/1984 | Sri Lanka . |
| 993584 | 5/1965 | United Kingdom . |
| 1108577 | 6/1965 | United Kingdom . |
| 1286225 | 8/1972 | United Kingdom . |

Primary Examiner—Michael L. Shippen
Attorney, Agent, or Firm—Morgan & Finnegan

[57] ABSTRACT

The invention provides compounds of the general formula (I)

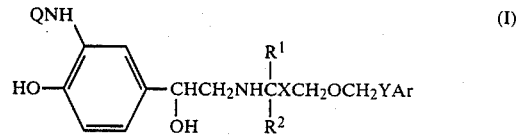

wherein Ar, $R^1$, $R^2$, X, Y and Q are defined in the specification and physiologically acceptable salts and solvates thereof.

The compounds have a selective stimulant action at $\beta_2$-adrenoreceptors and may be used, inter alia, in the treatment of diseases associated with reversible airways obstruction such as asthma and chronic bronchitis.

16 Claims, No Drawings

AMINOPHENOL DERIVATIVES

This application is a continuation-in-part of application Ser. No. 788,120, filed Oct. 16, 1985, now abandoned.

This invention relates to aminophenol derivatives having a stimulant action at $\beta_2$-adrenoreceptors, to processes for their preparation, to pharmaceutical compositions containing them and to their use in medicine.

Aminophenol derivatives possessing a sulphonamido or ureido substituent in the phenol ring have previously been described as bronchodilators having stimulant activity at $\beta$-adrenoreceptors.

Thus British Patent Specification No. 993584 describes compounds of the general structure

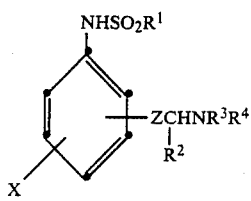

in which $R^1$ represents lower alkyl, phenyl or tolyl; X represents inter alia hydroxy; Z represents inter alia —CH(OH)—; $R^2$ and $R^3$ each represent inter alia hydrogen; and $R^4$ represents hydrogen, lower alkyl, or aralkyl or aryloxyalkyl in which the aryl ring may optionally be substituted by hydroxy, methoxy or methylenedioxy.

British Patent Specification No. 1286225 describes compounds of the general structure

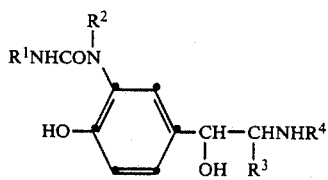

in which $R^1$ represents hydrogen, $C_{1-5}$ alkyl, phenyl, dimethylaminoethyl or dimethylaminopropyl; $R^2$ and $R^3$ each represent inter alia hydrogen; and $R^4$ represents $C_{3-5}$ alkyl, $C_{3-6}$ cycloalkyl, $C_{3-6}$ cycloalkylmethyl or the group

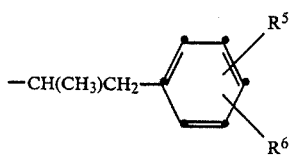

where $R^5$ and $R^6$ each represent hydrogen, hydroxy or methoxy.

We have now found a novel group of aminophenol derivatives, which differ structurally from those described in British Patent Specification Nos. 993584 and 1286225, and which have a desirable and useful profile of activity.

Thus, the present invention provides compounds of the general formula (I)

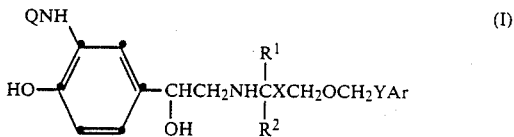

wherein

Ar represents a phenyl group optionally substituted by one or more substituents selected from halogen atoms, or the groups $C_{1-6}$alkyl, $C_{1-6}$alkoxy, nitro, —(CH$_2$)$_q$R, [where R is hydroxy, —NR$^3$R$^4$ (where $R^3$ and $R^4$ each represents a hydrogen atom, or a $C_{1-4}$ alkyl group, or —NR$^3$R$^4$ forms a saturated heterocyclic amino group which has 5–7 ring members and optionally contains in the ring one or more atoms selected from —O— or —S— or a group —NH— or —N(CH$_3$)—), —NR$^5$COR$^6$ (where $R^5$ represents a hydrogen atom or a $C_{1-4}$ alkyl group, and $R^6$ represents a hydrogen atom or a $C_{1-4}$ alkyl, $C_{1-4}$ alkoxy, phenyl or —NR$^3$R$^4$ group), —NR$^5$SO$_2$R$^7$ (where $R^7$ represents a $C_{1-4}$ alkyl, phenyl or —NR$^3$R$^4$ group), —COR$^8$ (where $R^8$ represents hydroxy, $C_{1-4}$ alkoxy or —NR$^3$R$^4$), —SR$^9$ (where $R^9$ is a hydrogen atom, or a $C_{1-4}$ alkyl or phenyl group), —SOR$^9$, —SO$_2$R$^9$, or —CN, and q represents an integer from 0 to 3], —(CH$_2$)$_r$R$^{10}$, [where $R^{10}$ is a $C_{1-4}$ alkoxy group and r represents an integer from 1 to 3], or —O(CH$_2$)$_t$R$^{11}$ [where $R^{11}$ represents a hydroxy or $C_{1-4}$ alkoxy group and t is 2 or 3], or Ar is a phenyl group substituted by an alkylenedioxy group of formula —O(CH$_2$)$_p$O—, where p represents 1 or 2;

$R^1$ and $R^2$ each represent a hydrogen atom or a $C_{1-3}$ alkyl group with the proviso that the sum total of carbon atoms in $R^1$ and $R^2$ is not more than 4;

X represents a $C_{1-7}$ alkylene, $C_{2-7}$ alkenylene or $C_{2-7}$ alkynylene chain;

Y represents a bond, or a $C_{1-6}$ alkylene, $C_{2-6}$ alkenylene or $C_{2-6}$ alkynylene chain with the proviso that the sum total of carbon atoms in X and Y is 2 to 10;

Q represents a group R$^{12}$CO—, R$^{12}$NHCO—, R$^{12}$R$^{13}$NSO$_2$— or R$^{14}$SO$_2$, where $R^{12}$ and $R^{13}$ each represent a hydrogen atom or a $C_{1-3}$ alkyl group, and $R^{14}$ represents a $C_{1-4}$ alkyl group; with the proviso that when X represents $C_{1-7}$ alkylene, and Y represents a bond or $C_{1-6}$ alkylene, then the group Ar does not represent an unsubstituted phenyl group or a phenyl group substituted by one or more substituents selected solely from halogen atoms or $C_{1-6}$ alkyl or $C_{1-6}$ alkoxy groups or an alkylenedioxy group —O(CH$_2$)$_p$O—; and physiologically acceptable salts and solvates (e.g. hydrates) thereof.

It will be appreciated that the compounds of general formula (I) possess one or two asymmetric carbon atoms, namely the carbon atom of the

group and, when $R^1$ and $R^2$ are different groups, the carbon atom to which these are attached.

The compounds according to the invention thus include all enantiomers, diastereoisomers and mixtures thereof, including racemates. Compounds in which the carbon atom in the

group is in the R configuration are preferred.

In the definition of general formula (I), the term alkenylene includes both cis and trans structures.

In one aspect, the invention provides compounds of formula (I) in which $R^1$—$R^{11}$, X, Y and Ar are as defined in formula (I) and Q represents the group $R^{12}CO$—, $R^{12}NHCO$— or $R^{14}SO_2$— where $R^{12}$ is as defined in formula (I) and $R^{14}$ represents a $C_{1-3}$ alkyl group.

In the general formula (I), the chain X may for example contain 2 to 7 carbon atoms and may be for example —$(CH_2)_2$—, —$(CH_2)_3$—, —$(CH_2)_4$—, —$(CH_2)_5$—, —$CH_2C\equiv C$—, —$(CH_2)_2CH\!=\!CH$—, —$(CH_2)_2C\equiv C$—, —$CH\!=\!CHCH_2$—, —$CH\!=\!CH(CH_2)_2$— or —$CH_2C\equiv CCH_2$—. The chain Y may be for example —$CH_2$—, —$(CH_2)_2$—, —$(CH_2)_3$—, —$(CH_2)_4$—, —$(CH_2)_5$—, —$(CH_2)_6$—, —$CH\!=\!CH$—, —$C\equiv C$—, —$CH_2CH\!=\!CH$—, or —$CH_2C\equiv C$—.

In general, the total number of carbon atoms in the chains X and Y is preferably 4 to 10 inclusive and may be for example 5, 6, 7 or 8. Compounds wherein the sum total of carbon atoms in the chains X and Y is 5, 6, or 7 are particularly preferred.

One preferred group of compounds of formula (I) is that in which X is $C_{1-7}$ alkylene, Y is $C_{1-6}$ alkylene and Q, Ar, $R^1$ and $R^2$ are as defined for formula (I). Particularly interesting compounds of this type are those in which X is —$(CH_2)_2$—, —$(CH_2)_3$—, —$(CH_2)_4$ or —$(CH_2)_5$—, particularly —$(CH_2)_3$— or —$(CH_2)_4$—, and Y is —$CH_2$—, —$(CH_2)_2$—, —$(CH_2)_3$—, —$(CH_2)_4$— or —$(CH_2)_5$—, particularly —$CH_2$—, —$(CH_2)_2$— or —$(CH_2)_3$—.

Another preferred group of compounds of formula (I) is that in which X is —$(CH_2)_2$—, —$(CH_2)_3$—, —$(CH_2)_4$— or —$(CH_2)_5$—, particularly —$(CH_2)_3$— or —$(CH_2)_4$— and Y is a $C_{2-3}$ alkenylene or $C_{2-3}$ alkynylene group, particularly —$CH_2CH\!=\!CH$— or —$CH_2C\equiv C$—.

A further preferred group of compounds of formula (I) is that in which X is a $C_{3-4}$ alkynylene group, particularly —$CH_2C\equiv CCH_2$—, and Y is —$CH_2$—, —$(CH_2)_2$—, —$(CH_2)_3$—, —$(CH_2)_4$— or —$(CH_2)_5$—, particularly —$(CH_2)_3$—.

In the compounds of formula (I) $R^1$ and $R^2$ may each be, for example, methyl, ethyl, propyl or isopropyl groups except that if one of $R^1$ and $R^2$ is a propyl or isopropyl group, the other is a hydrogen atom or a methyl group. Thus for example $R^1$ may be a hydrogen atom or a methyl, ethyl or propyl group. $R^2$ may be for example a hydrogen atom or a methyl group. $R^1$ and $R^2$ are each preferably a hydrogen atom or a methyl group. A preferred group of compounds is that wherein $R^1$ and $R^2$ are both hydrogen atoms, or $R^1$ is a hydrogen atom and $R^2$ is a $C_{1-3}$ alkyl group, particularly a methyl group, or $R^1$ is a methyl group and $R^2$ is a methyl group.

In the group Q, $R^{12}$ and $R^{13}$ may each be for example, a hydrogen atom or a methyl, ethyl, propyl or isopropyl group, and $R^{14}$ may be for example a methyl, ethyl, propyl, isopropyl or butyl group. Preferably $R^{12}$ represents hydrogen or methyl, $R^{13}$ represents methyl, and $R^{14}$ represents methyl. Preferred meanings for the group Q are $HCO$—, $CH_3CO$—, $NH_2CO$—, $(CH_3)_2NSO_2$— and $CH_3SO_2$—, more preferably $HCO$—, $NH_2CO$— or $CH_3SO_2$—. Compounds in which Q represents $R^{14}SO_2$— where $R^{14}$ is methyl are particularly preferred.

When —$NR^3R^4$ in compounds of formula (I) represents a saturated heterocyclic amino group, this may have 5, 6 or 7 ring members and optionally contain in the ring a heteroatom selected from —O—, or —S—, or a group —NH— or —N(CH$_3$)—. Examples of such —$NR^3R^4$ groups are pyrrolidino, piperidino, hexamethylenimino, piperazino, N-methylpiperazine, morpholino, homomorpholino or thiamorpholino.

Ar may be for example a phenyl group. Examples of the optional substituents which may be present on the phenyl group represented by Ar include chlorine, bromine, iodine, fluorine, methyl, ethyl, methoxy, ethoxy, —$(CH_2)_qR$ [where R is hydroxy, amino, methylamino, ethylamino, dimethylamino, diethylamino, morpholino, piperidino, piperazino, N-methylpiperazino, —$NHCOR^6$ (where $R^6$ is hydrogen or a $C_{1-4}$ alkyl (e.g. methyl, ethyl, isopropyl or n-butyl), $C_{1-4}$ alkoxy (e.g. methoxy, ethoxy, isopropoxy or n-butoxy), phenyl, amino or N,N-dimethylamino), —$N(CH_3)COCH_3$—, —$NHSO_2CH_3$, —$NHSO_2(CH_2)_3CH_3$, —$NR^5SO_2R^7$, (where $R^5$ represents a hydrogen atom or a methyl group and $R^7$ represents phenyl), —$NHSO_2NH_2$, —$NHSO_2N(CH_3)_2$, —$COOH$, —$COOCH_3$, —$COOCH_2CH_2CH_3$, —$CONH_2$, —$CON(CH_3)_2$, —$CON(CH_2CH_3)_2$, —$CON(CH_2CH_2CH_3)_2$,

—$SR^9$ (where $R^9$ is methyl, ethyl or phenyl) —$SOCH_3$, —$SO_2CH_3$, or CN, and q is zero, 1, 2 or 3], —$NO_2$, —$CH_2OCH_3$, —$(CH_2)_3OCH_3$, —$O(CH_2)_2OH$, —$O(CH_2)_3OH$, —$O(CH_2)_2OCH_3$, or —$O(CH_2)_2OCH_2CH_3$.

The phenyl group represented by Ar may optionally contain one, two or three substituents, which may be present at the 2-, 3-, 4-, 5- or 6-positions on the phenyl ring.

Particular examples of a trisubstituted phenyl group represented by Ar include phenyl substituted by an amino and two methyl groups (for example 3,5-dimethyl-4-aminophenyl), an amino group and two chlorine atoms (for example 3,5-dichloro-4-aminophenyl), or three methoxy groups (for example 3,4,5-trimethoxyphenyl). Particular examples of a disubstituted phenyl group represented by Ar include phenyl substituted by two hydroxyl groups (for example 3,5-dihydroxyphenyl), a hydroxyl and methoxy group (for example 3-methoxy-4-hydroxyphenyl), or two methyl groups (for example 3,4-dimethylphenyl).

In general, when the substituent on the phenyl group represented by Ar is one of the groups —$(CH_2)_qR$, where R is —$NR^3R^4$, —$NR^5COR^6$, —$NR^5SO_2R^7$, —$COR^8$, —$SR^9$, —$SOR^9$, —$SO_2R^9$ or —CN and q is an integer 1, 2 or 3, any additional substituent present on the phenyl group is desirably one which is different from those substituents.

A preferred group of compounds are those of formula (Ia)

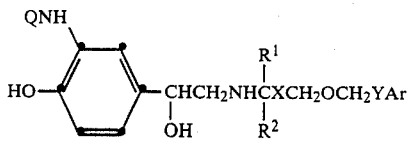

(Ia)

and physiologically acceptable salts and solvates thereof wherein X represents a $C_{1-7}$ alkylene, $C_{2-7}$ alkenylene or $C_{2-7}$ alkynylene chain, Y represents a bond or a $C_{1-6}$ alkylene, $C_{2-6}$ alkenylene or $C_{2-6}$ alkynylene chain, and the sum total of carbon atoms in the chains X and Y is 5,6 or 7; $R^1$ and $R^2$ each represent a hydrogen atom or a methyl group; Q represents HCO—, $NH_2CO$—, $(CH_3)_2NSO_2$— or $CH_3SO_2$—; and Ar represents a phenyl group substituted by a group selected from amino, dimethylamino, nitro, morpholino, —$(CH_2)_qNHCOR^6$ (where $R^6$ is $C_{1-4}$ alkyl e.g. n-butyl and q is zero or more preferably 1), —$NHSO_2R^7$ (where $R^7$ is $C_{1-4}$ alkyl e.g. butyl), —$COR^8$ (where $R^8$ is $C_{1-4}$ alkoxy, e.g. propoxy, or —$NR^3R^4$ where $R^3$ and $R^4$ are both $C_{1-4}$ alkyl e.g. ethyl or propyl, or $NR^3R^4$ forms a piperidino ring), —$CH_2CONR^3R^4$ (where $R^3$ and $R^4$ are both $C_{1-4}$ alkyl e.g. ethyl), —$SR^9$ (where $R^9$ is $C_{1-4}$ alkyl e.g. methyl) or —$(CH_2)_rR^{10}$ (where r is 3 and $R^{10}$ is $C_{1-4}$ alkoxy e.g. methoxy), or Ar is 3,5-dihydroxyphenyl or 3-methoxy-4-hydroxyphenyl, or when X and/or Y represent an alkenylene or alkynylene group then Ar may additionally represent a phenyl group optionally substituted by a fluorine atom.

A particularly preferred group of compounds of formula (Ia) are those in which X represents a $C_{3-4}$ alkylene group and Y represents a $C_{1-3}$ alkylene group, or X represents a $C_4$ alkynylene group (e.g. —$CH_2C\equiv CCH_2$) and Y represents a $C_3$ alkylene group, or X represents a $C_{3-4}$ alkylene group and Y represents a $C_3$ alkenylene or $C_3$ alkynylene group (e.g. —$CH_2CH=CH$— or —$CH_2C\equiv C$—). Most preferably X represents —$(CH_2)_4$— and Y represents —$(CH_2)_3$—.

Another particularly preferred group of compounds of formula (Ia) are those in which Q represents $CH_3SO_2$—.

A further particularly preferred group of compounds of formula (Ia) are those in which Ar represents a phenyl group optionally substituted by an amino, nitro, $CH_2NHCO(CH_2)_3CH_3$ or —$CON(CH_2CH_3)_2$ group, or by hydroxyl groups at the 3- and 5- positions. Most preferably Ar is a phenyl group containing a single substituent, preferably —$CON(CH_2CH_3)_2$.

Particularly important compounds of the invention are:

N,N-diethyl-4-[4-[[6-[[2-hydroxy-2-[4-hydroxy-3-[(methyl sulphonyl)amino]phenyl]ethyl]amino]hexyl]oxy]butyl]benzamide;

N-[2-hydroxy-5-[1-hydroxy-2-[[6-[4-(3,5-dihydroxyphenyl)butoxy]hexyl]amino]ethyl]phenyl]methanesulphonamide;

N-[2-hydroxy-5-[1-hydroxy-2-[[6-[4-(4-hydroxy-3-methoxyphenyl)butoxy]hexyl]amino]ethyl]phenyl]methanesulphonamide;

N-[2-hydroxy-5-[1-hydroxy-2-[[6-[4-(4-(methylthio)phenyl]butoxy]hexyl]amino]ethyl]phenyl]methanesulphonamide;

N-[2-hydroxy-5-[1-hydroxy-2-[[6-[4-(4-nitrophenyl)butoxy]hexyl]amino]ethyl]phenyl]methanesulphonamide;

N-[5-[2-[[6-[4-(4-aminophenyl)butoxy]hexyl]amino-1-hydroxyethyl]-2-hydroxyphenyl]methanesulphonamide; propyl-4-[4-[[5-[[2-hydroxy-2-[4-hydroxy-3-[(methylsulphonyl)amino]phenyl]ethyl]amino]pentyl]oxy]butyl]benzoate;

N-[[4-[4-[[6-[[2-hydroxy-2-[4-hydroxy-3-[(methylsulphonyl)amino]phenyl]ethyl]amino]hexyl]oxy]butyl]phenyl]methyl]pentanamide;

N-[2-hydroxy-5-[1-hydroxy-2-[[5-[4-[4-(3-methoxypropyl)phenyl]butoxy]pentyl]amino]ethyl]phenyl]formamide;

N-[4-[4-[[6-[[2-[3-[(aminocarbonyl)amino]-4-hydroxyphenyl]ethyl]amino]hexyl]oxy]butyl]phenyl]butanesulphonamide;

N-[2-hydroxy-5-[1-hydroxy-2-[[6-(4-phenylbutoxy)-3-hexynyl]amino]ethyl]phenyl]methanesulphonamide;

(E)-N-[2-hydroxy-5-[1-hydroxy-2-[[6-[[4-(4-fluorophenyl)-3-butenyl]oxy]hexyl]amino]ethyl]phenyl]methanesulphonamide;

and their physiologically acceptable salts and hydrates.

Suitable physiologically acceptable salts of the compounds of general formula (I) include acid addition salts derived from inorganic and organic acids, such as hydrochlorides, hydrobromides, sulphates, phosphates, maleates, tartrates, citrates, benzoates, 4-methoxybenzoates, 2- or 4-hydroxybenzoates, 4-chlorobenzoates, p-toluenesulphonates, methanesulphonates, sulphamates, ascorbates, salicylates, acetates, fumarates, succinates, lactates, glutarates, gluconates, tricarballylates, hydroxynaphthalenecarboxylates e.g. 1-hydroxy- or 3-hydroxy-2-naphthalenecarboxylates, or oleates. The compounds may also form salts with suitable bases. Examples of such salts are alkali metal (e.g. sodium and potassium), and alkaline earth metal (e.g. calcium or magnesium) salts.

The compounds according to the invention have a selective stimulant action at $\beta_2$-adrenoreceptors, which furthermore is of a particularly advantageous profile. The stimulant action was demonstrated in the isolated trachea of the guinea-pig, where compounds were shown to cause relaxation of PGF2α-induced contractions. Compounds according to the invention have shown a particularly long duration of action in this test.

The compounds according to the invention may be used in the treatment of diseases associated with reversible airways obstruction such as asthma and chronic bronchitis.

The compounds according to the invention may also be used for the treatment of premature labour, depression and congestive heart failure, and are also indicated as useful for the treatment of inflammatory and allergic skin diseases, glaucoma, and in the treatment of conditions in which there is an advantage in lowering gastric acidity, particularly in gastric and peptic ulceration.

The invention accordingly further provides compounds of formula (I) and their physiologically acceptable salts and solvates for use in the therapy or prophylaxis of diseases associated with reversible airways obstruction in human or animal subjects.

The compounds according to the invention may be formulated for administration in any convenient way. The invention therefore includes within its scope pharmaceutical compositions comprising at least one compound of formula (I) or a physiologically acceptable salt of solvate thereof formulated for use in human or veterinary medicine. Such compositions may be presented for use with physiologically acceptable carriers or excipients, optionally with supplementary medicinal agents.

The compounds may be formulated in a form suitable for administration by inhalation or insufflation, or for oral, buccal, parenteral, topical (including nasal) or rectal administration. Administration by inhalation or insufflation is preferred.

For administration by inhalation the compounds according to the invention are conveniently delivered in the form of an aerosol spray presentation from pressurised packs, with the use of a suitable propellant, such as dichlorodifluoromethane, trichlorofluoromethane, dichlorotetrafluoroethane, carbon dioxide or other suitable gas, or from a nebuliser. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in for example capsules or cartridges of e.g. gelatin, or blister packs from which the powder may be administered with the aid of an inhaler or insufflator.

For oral administration, the pharmaceutical composition may take the form of, for example, tablets, capsules, powders, solutions, syrups or suspensions prepared by conventional means with acceptable excipients.

For buccal administration the composition may take the form of tablets, drops or lozenges formulated in conventional manner.

The compounds of the invention may be formulated for parenteral administration by bolus injection or continuous infusion. Formulations for injection may be presented in unit dosage form in ampoules, or in multi-dose containers with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water, before use.

For topical administration the pharmaceutical composition may take the form of ointments, lotions or creams formulated in a conventional manner, with for example an aqueous or oily base, generally with the addition of suitable thickening agents and/or solvents. For nasal application, the composition may take the form of a spray, formulated for example as an aqueous solution or suspension or as an aerosol with the use of a suitable propellant.

The compounds of the invention may also be formulated in rectal compositions such as suppositories or retention enemas, e.g. containing conventional suppository bases such as cocoa butter or other glyceride.

Where pharmaceutical compositions are described above for oral, buccal, rectal or topical administration, these may be presented in a conventional manner associated with controlled release forms.

A proposed daily dosage of active compound for the treatment of man is 0.005 mg to 100 mg, which may be conveniently administered in one or two doses. The precise dose employed will of course depend on the age and condition of the patient and on the route of administration. Thus a suitable dose for administration by inhalation is 0.005 mg to 20 mg, for oral administration is 0.02 mg to 100 mg, and for parenteral administration is 0.01 mg to 2 mg for administration by bolus injection and 0.01 mg to 25 mg for administration by infusion.

The compounds according to the invention may be prepared by a number of processes, as described in the following wherein Q, X, Y, Ar, $R^1$ and $R^2$ are as defined for general formula (I) unless otherwise specified. It will be appreciated that certain of the reactions described below are capable of affecting other groups in the starting material which are desired in the end product; this applies especially in the reduction processes described, particularly where a hydride reducing agent is used and end-products are required in which Q represents the group $R^{12}CO$, and where hydrogen and a metal catalyst are used in the preparation of compounds containing an ethylene or acetylene linkage. Care must therefore be taken in accordance with conventional practice, either to use reagents which will not affect such groups, or to perform the reaction as part of a sequence which avoids their use when such groups are present in the starting material. In the general processes described below for the preparation of both intermediates and end-products the final step in the reaction may be the removal of a protecting group. Suitable protecting groups and their removal are described in general process (2) below.

According to one general process (1), a compound of general formula (I) may be prepared by alkylation. Conventional alkylation procedures may be used.

Thus, for example, in one process (a), a compound of general formula (I) in which $R^1$ is a hydrogen atom may be prepared by alkylation of an amine of general formula (II)

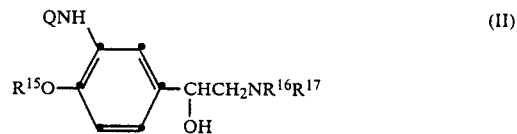
(II)

(where each of $R^{15}$ and $R^{16}$ is a hydrogen atom or a protecting group and $R^{17}$ is a hydrogen atom) followed by removal of any protecting group where present.

The alkylation (a) may be effected using an alkylating agent of general formula (III):

(III)

(wherein L represents a leaving group, for example a halogen atom such as chlorine, bromine or iodine, or a hydrocarbylsulphonyloxy group such as methanesulphonyloxy or p-toluenesulphonyloxy).

The alkylation is preferably effected in the presence of a suitable acid scavenger, for example, inorganic bases such as sodium or potassium carbonate, organic bases such as triethylamine, diisopropylethylamine or pyridine, or alkylene oxides such as ethylene oxide or propylene oxide. The reaction is conveniently effected in a solvent such as acetonitrile or an ether e.g. tetrahydrofuran or dioxan, a ketone e.g. butanone or methyl isobutyl ketone, a substituted amide e.g. dimethylformamide or a chlorinated hydrocarbon e.g. chloroform at a temperature between ambient and the reflux temperature of the solvent.

According to another example (b) of an alkylation process, a compound of general formula (I) in which $R^1$ represents a hydrogen atom may be prepared by alkylation of an amine of general formula (II), as previously defined except that $R^{17}$ is a hydrogen atom or a group convertible thereto under the reaction conditions, with a compound of general formula (IV):

R²COXCH₂OCH₂YAr    (IV)

in the presence of a reducing agent, followed when necessary by removal of any protecting groups.

Examples of suitable $R^{17}$ groups convertible into a hydrogen atom are arylmethyl groups such as benzyl, α-methylbenzyl and benzhydryl.

Suitable reducing agents include hydrogen in the presence of a catalyst such as platinum, platinum oxide, palladium, palladium oxide, Raney nickel or rhodium, on a support such as charcoal, using an alcohol, e.g. ethanol or an ester e.g. ethyl acetate or an ether e.g. tetrahydrofuran, or water, as reaction solvent, or a mixture of solvents, e.g. a mixture of two or more of those just described at normal or elevated temperature and pressure, for example from 20° to 100° C. and from 1 to 10 atmospheres.

Alternatively when one or both of $R^{16}$ and $R^{17}$ are hydrogen atoms, the reducing agent may be a hydride such as diborane or a metal hydride such as sodium borohydride, sodium cyanoborohydride or lithium aluminium hydride. Suitable solvents for the reaction with these reducing agents will depend on the particular hydride used, but will include alcohols such as methanol or ethanol, or ethers such as diethyl ether or tert-butyl methyl ether, or tetrahydrofuran.

When a compound of formula (II) where $R^{16}$ and $R^{17}$ are each hydrogen atoms are used, the intermediate imine of formula (V) may be formed:

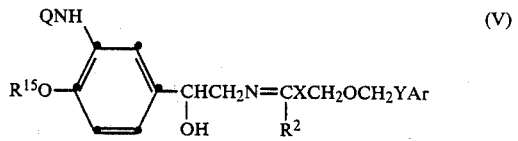

(wherein $R^{15}$ is as defined for formula (II)).

Reduction of the imine using the conditions described above, followed, where necessary, by removal of any protecting groups, gives a compound of general formula (I).

Where it is desired to use a protected intermediate of general formula (II) it is particularly convenient to use hydrogen and a catalyst as described above with protecting groups $R^{15}$ and $R^{16}$ which are capable of being converted to a hydrogen atom under these reducing conditions, thus avoiding the need for a separate deprotection step. Suitable protecting groups of this type include arylmethyl groups such as benzyl, benzhydryl and α-methylbenzyl.

In another general process (2), a compound of general formula (I) may be obtained by deprotection of a protected intermediate of general formula (VI):

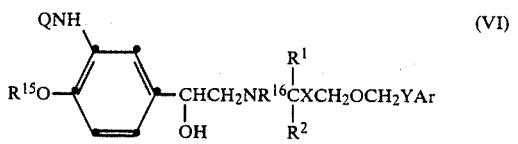

(where $R^{15}$ and $R^{16}$ are as defined in formula (II) except that at least one of $R^{15}$ and $R^{16}$ is a protecting group).

The protecting group may be any conventional protecting group, for example as described in "Protective Groups in Organic Chemistry", Ed. J. F. W. McOmie (Plenum Press, 1973). Examples of suitable hydroxyl protecting groups represented by $R^{15}$ are arylmethyl groups such as benzyl, diphenylmethyl or triphenylmethyl and tetrahydropyranyl. Examples of suitable amino protecting groups represented by $R^{16}$ are arylmethyl groups such as benzyl, α-methylbenzyl, diphenylmethyl or triphenylmethyl and acyl groups such as trichloroacetyl or trifluoroacetyl.

The deprotection to yield a compound of general formula (I) may be effected using conventional techniques. Thus for example, when $R^{15}$ and/or $R^{16}$ is an arylmethyl group this may be cleaved by hydrogenolysis in the presence of a metal catalyst (e.g. palladium on charcoal). When $R^{15}$ is tetrahydropyranyl this may be cleaved by hydrolysis under acidic conditions. Acyl groups represented by $R^{16}$ may be removed by hydrolysis, for example with a base such as sodium hydroxide, or a group such as trichloroacetyl may be removed by reduction with, for example, zinc and acetic acid.

In another general process (3), a compound of general formula (I) may be prepared by reduction. Thus, for example, a compound of general formula (I) may be prepared by reducing an intermediate of general formula (VII):

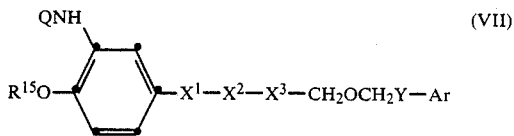

(where $R^{15}$ is as defined in formula (II) and at least one of $X^1$, $X^2$ and $X^3$ represents a reducible group, and/or Y and/or Ar contains a reducible group, and the other(s) take the appropriate meaning as follows, which is $X^1$ is —CH(OH)—, $X^2$ is —CH₂NR¹⁶ and $X^3$ is —CR¹R²X, followed where necessary by removal of any protecting groups.

Suitable reducible groups include those wherein $X^1$ is a group >C=O, $X^2$ is a group or —CH₂NY'—(wherein Y¹ represents a group convertible to hydrogen by catalytic hydrogenation, for example an arylmethyl group such as benzyl, benzhydryl or α-methylbenzyl), or an imine (—CH=N—) group or a group —CONH—, $X^3$ is a group —COX— or a group —CR¹R²X— (where X is $C_{2-7}$ alkenylene or $C_{2-7}$ alkynylene), or —X²—X³— is a group —CH₂N=CR²X—, Y is $C_{2-6}$ alkenylene or $C_{2-6}$ alkynylene, and Ar is a phenyl group substituted by a nitro group. In one convenient aspect of the reduction process, the group $R^{15}$ may be a group convertible to hydrogen under the reducing conditions employed and may be for example an arylmethyl group such as benzyl, benzhydryl or α-methylbenzyl.

The reduction may be effected using reducing agents conveniently employed for the reduction of ketones, imines, amides, protected amines, alkenes, alkynes and nitro groups.

Thus, for example, when the phenyl group Ar contains a nitro substituent, this may be reduced to an amino group using hydrogen in the presence of a catalyst as previously described for process (1) part (b).

When $X^1$ in general formula (VII) represents a >C=O group this may be reduced to a —CH(OH)— group using hydrogen in the presence of a catalyst as previously described for process (1) part (b). Alternatively, the reducing agent may be, for example, a hydride such as diborane or a metal hydride such as lithium aluminium hydride, sodium bis(2-methoxyethoxy) aluminium hydride, sodium borohydride or aluminium hydride. The reaction may be effected in a solvent, where appropriate an alcohol e.g. methanol or ethanol, or an ether such as tetrahydrofuran, or a halogenated hydrocarbon such as dichloromethane.

When $X^2$ in general formula (VII) represents a —CH$_2$NY$^1$— group or the group —CH=N—, or $X^2$—$X^3$ represents —CH$_2$N=CR$^2$X— this may be reduced to a —CH$_2$NH— or —CH$_2$NHCHR$^2$X— group using hydrogen in the presence of a catalyst as previously described for process (1) part (b). Alternatively, when $X^2$ is the group —CH=N— or —$X^2$—$X^3$— is the group or —CH$_2$N=CR$^2$X— this may be reduced to a —CH$_2$NH— or —CH$_2$NHCHR$^2$X— group using a reducing agent and conditions as just described for the reduction of $X^1$ when this represents a >C=O group.

When $X^2$ or $X^3$ in general formula (VII) represents a —CONH— or —COX— group this may be reduced to a group —CH$_2$NH— or —CH$_2$X— using a hydride such as diborane or a complex metal hydride such as lithium aluminium hydride or sodium bis(2-methoxyethoxy)aluminium hydride in a solvent such as an ether, e.g. tetrahydrofuran or diethyl ether.

When $X^3$ in general formula (VII) represents a group —CR$^1$R$^2$X— where X is C$_{2-7}$ alkenylene or C$_{2-7}$ alkynylene, or Y represents C$_{2-6}$ alkenylene or C$_{2-6}$ alkynylene, X and/or Y may be reduced to C$_{2-7}$ alkylene using hydrogen in the presence of a catalyst as previously described for process (1) part (b). Alternatively, when X and/or Y is C$_{2-7}$ alkynylene this may be reduced to C$_{2-7}$ alkenylene using for example hydrogen and a lead-poisoned palladium on calcium carbonate catalyst in a solvent such as pyridine, or lithium aluminium hydride in a solvent such as diethyl ether at a low temperature e.g. 0° C.

It is also possible to prepare a compound of general formula (I) by a process comprising interconversion of one compound of general formula I into another compound of general formula (I).

For example, a compound of formula (I) in which Ar is phenyl substituted by a nitro group may be converted to the corresponding compound in which Ar is phenyl substituted by an amino group by reduction. Conventional reducing agents may be used, for example hydrogen in the presence of a catalyst such as platinum or palladium on a support such as charcoal, in a solvent such as an alcohol e.g. ethanol.

In another example, a compound of formula (I) in which Ar is phenyl substituted by —(CH$_2$)$_q$CONR$^3$R$^4$ (where q is zero, 1 or 2) may be reduced to a compound of formula (I) in which Ar is phenyl substituted by —(CH$_2$)$_q$NR$^3$R$^4$, where q is 1, 2 or 3. The reduction may be performed using a hydride such as diborane, or a complex metal hydride such as lithium aluminium hydride or sodium bis(2-methoxyethoxy)aluminum hydride in a solvent such as an ether e.g. tetrahydrofuran or diethyl ether.

In another example, a compound of formula (I) in which X and/or Y is an alkenylene or alkynylene chain, may be reduced to a compound of formula (I) in which X and/or Y is an alkylene chain using hydrogen in the presence of a metal catalyst as previously described for process (1) part (b).

In a further example, a compound of formula (I) in which X and/or Y is an alkenylene chain may be prepared by reduction of a corresponding compound in which X and/or Y is an alkynylene chain as previously described under process (3).

In the general processes described above, the compound of formula (I) obtained may be in the form of a salt, conveniently in the form of a physiologically acceptable salt. Where desired, such salts may be converted to the corresponding free acids using conventional methods.

Physiologically acceptable salts of the compounds of general formula (I) may be prepared by reacting a compound of general formula (I) with an appropriate acid or base in the presence of a suitable solvent such as acetonitrile, acetone, chloroform, ethyl acetate or an alcohol, e.g. methanol, ethanol or iso-propanol.

Physiologically acceptable salts may also be prepared from other salts, including other physiologically acceptable salts, of the compounds of general formula (I), using conventional methods.

When a specific enantiomer of a compound of general formula (I) is required, this may be obtained by resolution of a corresponding racemate of a compound of general formula (I) using conventional methods.

Thus, in one example an appropriate optically active acid may be used to form salts with the racemate of a compound of general formula (I). The resulting mixture of isomeric salts may be separated for example by fractional crystallisation, into the diastereoisomeric salts from which the required enantiomer of a compound of general formula (I) may be isolated by conversion into the required free base.

Alternatively, enantiomers of a compound of general formula (I) may be synthesised from the appropriate optically active intermediates using any of the general processes described herein.

Specific diastereoisomers of a compound of formula (I) may be obtained by conventional methods for example, by synthesis from an appropriate asymmetric starting material using any of the processes described herein, or by conversion of a mixture of isomers of a compound of general formula (I) into appropriate diastereoisomeric derivatives e.g. salts which then can be separated by conventional means e.g. by fractional crystallisation.

Suitable methods for preparing the intermediate compounds used in the above general processes are described below. In the following discussion, Ar, R$^1$, R$^2$, R$^{15}$, R$^{16}$, R$^{17}$, Q, X, Y, X$^1$, X$^2$, X$_3$, Y$^1$, and L are as defined above except where otherwise indicated. "Hal" represents a halogen atom. Where an intermediate with protected hydroxyl and/or amino groups is desired, this may be obtained using conventional protection methods, for example those described by McOmie (see process (2) above). In addition, any substituent in Ar may be a precursor substituent which is convertible into the required substituent, for example as described above for the interconversion of compounds of formula (I).

Intermediate compounds of general formula (VII) for use in general process (3) may be prepared by a number of processes.

Thus for example intermediates of general formula (VII) in which $X^1$ is a group >C=O may be prepared from a haloketone of formula (IX):

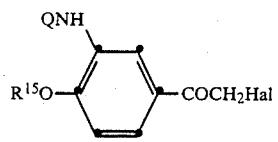

by reaction with an amine of general formula (X):

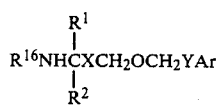

(where $R^{16}$ is a hydrogen atom or a group convertible thereto by catalytic hydrogenation).

The reaction may be effected in a cold or hot solvent, for example tetrahydrofuran, tert-butyl methyl ether, dioxan, chloroform, dimethylformamide, acetonitrile or a ketone such as butanone or methylisobutylketone, or an ester, for example ethyl acetate, preferably in the presence of a base such as diisopropylethylamine, sodium carbonate or other acid scavenger such as propylene oxide.

The intermediates of formulae (II) and (IX) are either known compounds or may be prepared according to the methods described by Kaiser et al in J. Med. Chem., 1974, 17, 49, and Larsen et al in J. Med. Chem., 1967, 10, 462.

Intermediates of general formula (VII) in which $X^1$ is a group $>C=O$ may be reduced to the corresponding intermediate in which $X^1$ is a group —CH(OH)— using for example a metal hydride such as sodium borohydride in a solvent e.g. ethanol.

Iminoketones of general formula (VII) in which $X^2$ is a group —CH=N— may be obtained from a phenylglyoxal derivative of formula (XI):

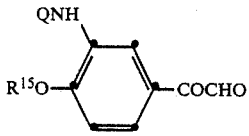

by reaction with an amine of formula (X) in which $R^{16}$ represents a hydrogen atom in a solvent such as benzene, tetrahydrofuran or an alcohol e.g. ethanol at temperatures up to the reflux. The phenylglyoxal derivatives of formula (XI) may be obtained from a haloketone of formula (IX) by the action of a dialkylsulphoxide such as dimethylsulphoxide.

Intermediates of general formula (VII) in which $X^3$ is a group —COX— may be prepared by acylation of an amine of formula (XII):

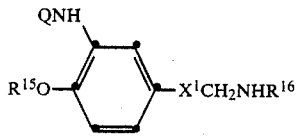

using an ester or an activated derivative of an acid of formula (XIII):

Suitable activated derivatives include the acid chloride, an anhydride or imidazolide. The reaction may be optionally carried out in a solvent such as tetrahydrofuran, benzene or chloroform, optionally in the presence of a base such as pyridine or triethylamine. The acids (XIII) may be used directly if a coupling agent such as dicyclohexylcarbodiimide is added.

Acids of formula (XIII) may be obtained by treatment of an alcohol of general formula (XIV)

with a suitable oxidising agent, for example pyridinium dichromate in a solvent such as dimethylformamide.

Intermediates of formula (VII) in which —$X^2$—$X^3$— represents —$CH_2N=CR^2X$— may be obtained by reaction of an amine of formula (XII) in which $R^{16}$ is a hydrogen atom with a compound of formula (IV) in a solvent such as acetonitrile.

Intermediates of formula (VII) in which $X^2$ is —CONH— may be prepared by reaction of an amine of formula (X) in which $R^{16}$ is a hydrogen atom with an acid of formula (XV):

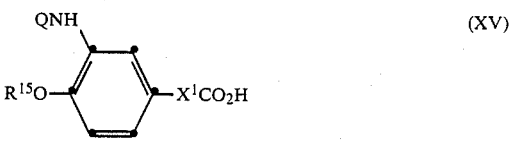

in the presence of a coupling agent such as dicyclohexylcarbodiimide. The acids of formula (XV) may be prepared by methods analogous to conventional methods for the preparation of α-keto- and α-hydroxy carboxylic acids.

Intermediates of formulae (III), (IV), (X) and (XIV) are either known compounds or may be prepared by methods analagous to those described for the preparation of known compounds. Suitable methods are described in UK Specification No. 2140800A and in the exemplification included hereinafter.

In addition, for the preparation of ketones of formula (IV) (in which $R^2$ represents an alkyl group), a halide $ArYCH_2OCH_2XHal$ (where X represents a bond, $C_{1-6}$ alkylene, $C_{2-6}$ alkenylene or $C_{2-6}$ alkynylene) may be reacted with an appropriate β-ketoester or β-diketone under basic conditions to give an alkylated derivative, which on hydrolysis affords a ketone of formula (IV).

The following examples illustrate the invention. Temperatures are in °C. 'Dried' refers to drying using magnesium sulphate or sodium sulphate except where otherwise stated. Thin layer chromatography (t.l.c.) was carried out over $SiO_2$. Flash column chromatography (FCC) was carried out on silica (Merck 9385). The following abbreviations are used: THF-tetrahydrofuran; EA-ethyl acetate, ER-diethyl ether; CX-cyclohexane; H-hexane; DMF-dimethylformamide; T-toluene; ET-ethanol; MC-methylene chloride; CF-chloroform; DEA-diisopropylethylamine; BTPC-bis(triphenylphosphine)palladium (II) chloride; A-0.88 Ammonia solution; DCC-dicyclohexylcarbodiimide; TAB-tetra-n-butylammonium sulphate; PT-C platinum on charcoal; PD-C palladium on charcoal; PTO-C platinum oxide on carbon; PDO-C palladium oxide on carbon.

INTERMEDIATE 1

[4-(3-Butynyloxy)butyl]benzene

A mixture of 3-butyn-1-ol (5.0 g), (4-bromobutyl)benzene (15.0 g), aqueous sodium hydroxide (30 ml, 50% w/v), and TAB (0.6 g) was stirred vigorously for 3 days, treated with water (100 ml) and extracted with ER (2×200 ml). The dried extract was evaporated and the residue was purified by FCC eluting with CX-ER 19:1 to give the title compound as a colourless oil (9.5 g). T.l.c. (CX-ER 9:1) Rf 0.45.

Similarly were prepared Intermediates 2–9

INTERMEDIATE 2

(E)-1-[[4-(6-Bromohexyl)oxy]-2-butenyl]-4-fluorobenzene as a yellow oil (8.49 g). T.l.c. (CX-EA) Rf 0.34.

From Intermediate 24 (5.73 g), 1,6-dibromohexane (25.2 g), TAB (1.5 g) and 40% NaOH (45 ml) except that the mixture was purified by FCC eluting with CX-EA (10:0→9:1).

INTERMEDIATE 3

1-[4-[(6-Bromohexyl)oxy]butyl]-4-nitrobenzene as a colourless liquid (1.92 g)

Analysis Found: C, 54.05; H, 6.95; N, 4.15; Br, 22.4; $C_{16}H_{24}BrNO_3$ requires C, 53.65; H, 6.75; N, 3.9; Br, 22.3%

From 4-nitrobenzenebutanol (2.00 g), 1,6-dibromohexane (4.73 ml), TAB (459 mg) and aq. sodium hydroxide (15.6 ml, 12.5M) except that the mixture was purified by FCC eluting with CX-ER (3:200→1:19).

INTERMEDIATE 4

3,5-Bis(phenylmethoxy)-1-[4-[(6-bromohexyl)oxy]-3-butenyl]benzene as a colourless oil (1.1 g).

Analysis Found: C, 68.95; H, 6.75. $C_{30}H_{35}BrO_3$ requires C, 68.8; H, 6.7%.

From Intermediate 30 (1.25 g), TAB (0.5 g), 1,6-dibromohexane (2.54 g) and 50% sodium hydroxide solution (10 ml) except that the mixture was purified by FCC eluting with CX and then CX-EA (9:1).

INTERMEDIATE 5

1-Bromo-6-[(3-butynyl)oxy]hexane as a colourless oil (27.0 g). T.l.c. (CX-ER 19:1) Rf 0.3

From 3-butyn-1-ol (20.0 g), 1,6-dibromohexane (209 g), aqueous sodium hydroxide (40% w/v; 100 ml) and TAB (2.0 g) except that the product was purified by FCC eluting with CX and then CX-ER (24:1).

INTERMEDIATE 6

1-[4-[(6-Bromohexyl)oxy]butyl]-4-(methylthio)benzene as a colourless oil (2.7 g). T.l.c. (CX-ER 19:1) Rf 0.3.

From 4-(methylthio)benzenebutanol (5.6 g), 1,6-dibromohexane (18.3 g), TAB (0.5 g) and aqueous sodium hydroxide (50% w/v, 20 ml).

INTERMEDIATE 7

1-Bromo-5-[(3-butynyl)oxy]pentane as a colourless oil (43.5 g). T.l.c. (CX-ER 9:1) Rf 0.65

From 3-butyn-1-ol (50.0 g), 1,5-dibromopentane (414 g), aqueous sodium hydroxide (50% w/v; 250 ml) and TAB (5.0 g) except that the product was purified by FCC eluting with CX and then CX-ER (9:1).

INTERMEDIATE 8

(E)-1-[4-[(6-Bromohexyl)oxy]-1-butenyl]-3-methoxy-4-(methoxymethoxy)benzene as a colourless oil (1.55 g). T.l.c. (CX-EA 3:1) Rf 0.50.

From Intermediate 32 (1.40 g), 1,6-dibromohexane (6.13 g), 50% aqueous sodium hydroxide (10 ml) and TAB (0.21 g) except that the mixture was extracted with EA (2×30 ml) and purified by FCC eluting with EA-H (1:19) followed by EA-H (1:4).

INTERMEDIATE 9

4-[4-[4-[(4-Bromobutoxy)]butyl]phenyl]morpholine as a colourless solid m.p. 33°–35°.

From Intermediate 34 (6.0 g), 1,4-dibromobutane (22.1 g), 50% aqueous sodium hydroxide (40 ml) and TAB (0.85 g) except that the reaction mixture was stirred under nitrogen for 20 h, and the product was purified by FCC eluting with CX and then ER-CX (1:3).

INTERMEDIATE 10

N-[4-[4-[[[6-(Phenylmethyl)amino]hexyl]oxy]butyl]phenyl]butanesulphonamide

Intermediate 16 (1.50 g) was added dropwise over 5 min to stirred benzylamine (1.79 g) at 120° under nitrogen. The solution was stirred at 120° under nitrogen for 2 h, then diluted with EA (50 ml) and washed with 2N hydrochloric acid (30 ml). The aqueous phase was re-extracted with EA (3×30 ml) and the combined organic extracts washed with 8% sodium bicarbonate solution (100 ml), dried and evaporated in vacuo to give the title compound as a yellow oil (1.32 g). T.l.c. (T-ET-A 39:10:1) Rf 0.49.

INTERMEDIATE 11

(E)-N-[6-[4-[(4-Hydroxy-3-methoxyphenyl)-3-butenyl]oxy]hexyl]benzenemethanamine as a brown oil (0.93 g) t.l.c. (T-ET-A 39:10:1) Rf 0.51 was prepared from Intermediate 29 (1 g) and benzylamine (1.5 g) following the method of Intermediate 10, except that MC was used for extraction instead of EA.

INTERMEDIATE 12

N-[5-[4-[4-(3-Methoxypropyl)phenyl]butoxy]pentyl]benzenemethanamine

Intermediate 18 (1.25 g) was added dropwise over 10 min to benzylamine (10 ml) stirred at 120° under nitrogen and stirring continued for a further 2 h. The mixture was cooled, poured into 2N hydrochloric acid (150 ml) and extracted with EA (1×75 ml, 1×50 ml). The combined organic layers were washed with 2N hydrochloric acid (50 ml), 8% sodium bicarbonate solution (100 ml), dried and concentrated in vacuo at 40° to afford the title compound as a pale yellow oil (1.06 g). T.l.c. (ER) Rf 0.38.

INTERMEDIATE 13

4-[4-[(6-Bromohexyl)oxy]-1-butynyl]-N,N-diethylbenzamide

A mixture of Intermediate 20 (10.0 g), Intermediate 5 (8.0 g) BTPC (0.5 g), cuprous iodide (0.059 g), DEA (50 ml) and THF (25 ml) was stirred at room temperature for 18 h, diluted with ER (100 ml), filtered and evaporated. The residue was purified by FCC eluting with CX-ER (1:1) to give the title compound as a yellow oil (12.5 g). T.l.c. (CX-ER 1:1) Rf 0.3.

Similarly were prepared intermediates 14–15

INTERMEDIATE 14

N-[4-[4-[(6-Bromohexyl)oxy]-1-butynyl]phenyl]-butanesulphonamide as a red oil (4.4 g). T.l.c. (H-EA 4:1) Rf 0.22.

From Intermediate 19 (5 g), Intermediate 5 (3.61 g), BTPC (300 mg), CuI (30 mg) and DEA (25 ml) except that purification was by FCC eluting with H-EA (9:1).

INTERMEDIATE 15

Propyl 4-[4-[(5-bromopentyl)oxy]-1-butynyl]benzoate as a colourless oil (5.8 g). T.l.c. (CX-ER 19:1) Rf 0.3.

From Intermediate 25 (10.0 g), Intermediate 7 (7.7 g), BTPC (0.35 g), CuI (0.035 g) and DEA (50 ml) except that the FCC eluting solvent was CX-ER (19:1).

INTERMEDIATE 16

N-[4-[4-[(6-Bromohexyl)oxy]butyl]phenyl]butanesulphonamide

Intermediate 14 (4.3 g) was hydrogenated in ET (40 ml) over pre-reduced 10% PDO-C (500 mg) and 5% PT-C (500 mg). The catalyst was removed by filtration through hyflo and the solvent was evaporated to give the title compound as a pale yellow oil (3.65 g). T.l.c. (H-EA 4:1) Rf 0.20

Similarly prepared were Intermediate 17–18

INTERMEDIATE 17

4-[4-[(6-Bromohexyl)oxy]butyl]-N,N-diethylbenzamide as a colourless oil (7.5 g). T.l.c. (ER-CX 1:1) Rf 0.3.

From Intermediate 13 (12.0 g), 10% PD-C (2 g) and 5% PT-C (2 g), purifying the product by FCC eluting with ER-CX (1:1).

INTERMEDIATE 18

1-[4-[(5-Bromopentyl)oxy]butyl]-4-(3-methoxypropyl)-benzene as a colourless oil (1.40 g). T.l.c. (ER-H 1:8) Rf 0.41.

From Intermediate 27 (3.0 g) and pre-reduced 10% PDO-C (1 g), purifying the product by FCC eluting with CX-ER (10:1).

INTERMEDIATE 19

N-(4-Iodophenyl)butanesulphonamide

Butanesulphonyl chloride (7.8 g) was added dropwise to a stirred solution of 4-iodobenzeneamine (10 g) in pyridine (50 ml) at 0°. The bright red mixture was stirred at room temperature for 1 h, then concentrated to an oil which was partitioned between 2N hydrochloric acid (100 ml) and EA (100 ml). The organic layer was washed with 2N hydrochloric acid, water and brine, dried (MgSO$_4$) and concentrated to a pale brown solid which was recrystallised from CX to give the title compound as white flakes (10.5 g) m.p. 80°–81°.

INTERMEDIATE 20

N,N-Diethyl-4-iodobenzamide

4-Iodobenzoyl chloride (10.0 g) was added portionwise to diethylamine (2.92 g) in triethylamine (40 ml) at 20°. The resulting slurry was stirred at room temperature for 1 h, diluted with ER (150 ml), filtered and evaporated to give the title compound as an orange solid (10.2 g) m.p. 68°–70°.

INTERMEDIATE 21

N,N-Dipropyl-4-iodobenzamide as an orange oil (11.51 g) t.l.c. (ER) Rf 0.48 was prepared from 4-iodobenzoyl chloride (10.0 g) and dipropylamine (4.10 g) according to the method of Intermediate 20.

INTERMEDIATE 22

N-[(4-Iodophenyl)methyl]pentanamide

Valeric anhydride (3.7 g) was added dropwise to 4-iodobenzene methanamine (4.2 g) and pyridine (3.2 g) in MC (50 ml) at 0°. The solution was stirred at 0° for 10 min and at room temperature for 2 h, washed with aqueous sodium bicarbonate, dried and evaporated. The residue was crystallised from ER at −78° to give the title compound as a white solid (3.7 g) m.p. 80°–81°.

INTERMEDIATE 23

1-Iodo-4-(3-methoxy-1-propynyl)benzene (i) 3-(4-iodophenyl)-2-propyn-1-ol

A mixture of 1,4-diiodobenzene (24.7 g), propargyl alcohol (1.68 g), BTPC (0.21 g) and CuI (28 mg) in diethylamine (180 ml) was stirred at room temperature under nitrogen for 18 h. The solvent was evaporated in vacuo at 35°, the residual solid taken up in MC (200 ml) and the solution washed with 2N hydrochloric acid (150 ml). The aqueous phase was extracted with further MC (75 ml), the organic layers combined, dried and purified by FCC eluting with EA-CX (1:6) and then EA-CX (1:3) to yield the title compound as a fawn crystalline solid (4.9 g) m.p. 101°–102°.

(ii) 1-Iodo-4-(3-methoxy-1-propynyl)benzene

Dimethylsulphate (2.2 g) was added dropwise over 5 min to a vigorously stirred mixture of the product of stage (i) (3.0 g), TAB (0.15 g) 50% w/v aqueous sodium hydroxide (2.8 ml) in H (10 ml) and MC (5 ml) and stirring was continued for a further 2.5 h. Concentrated ammonium hydroxide solution (5 ml) was added and the mixture was stirred for 30 min to destroy the excess dimethylsulphate. Water (50 ml) was added, the mixture extracted with ER (2×35 ml), the organic layer dried and concentrated in vacuo at 35° to afford a brown oil. This was purified by FCC eluting with ER-CX (1:10) yielding the title compound as a cream crystalline solid (2.91 g) m.p. ca20°. T.l.c. (ER-H 1:8) Rf 0.44.

INTERMEDIATE 24

(E)-4-[4-Fluorophenyl]-3-buten-1-ol n-Butyllithium (1.6M in H, 100 ml) was added dropwise to a stirred suspension of (3-hydroxypropyl)triphenylphosphonium bromide (32.1 g) in dry THF (200 ml) cooled to 0° C. under nitrogen. A solution of 4-fluorobenzaldehyde (9.93 g) in dry THF (100 ml) was added dropwise and the mixture stirred under nitrogen at 0° C. for 30 min and at room temperature for a further 1.5 h. The mixture was carefully diluted with water (25 ml), the solvent evaporated in vacuo at 40° and the residue partitioned between EA (200 ml) and water (200 ml). The aqueous phase was re-extracted with EA (200 ml), the organic phases combined, dried and evaporated in vacuo to give a brown oil. Purification by FCC eluting with CX-ER (1:1) gave the title compound as a colourless oil (6.33 g). T.l.c. (CX-ER 1:1) Rf 0.13

INTERMEDIATE 25

Propyl 4-iodobenzoate

DCC (13.4 g) was added in one portion to 4-iodobenzoic acid (15.0 g), n-propanol (7.2 g) and 4-(dimethylamino)pyridine (0.6 g) in MC (50 ml) at 0° under nitrogen. The mixture was stirred at 0° for 10 min and at room temperature for 3 h, diluted with ER (50 ml), filtered and evaporated. The residue was treated with CX (50 ml), filtered and the filtrate evaporated to give the title compound as a pale yellow oil (16.2 g). T.l.c. (CX-ER 3:1) Rf 0.8.

INTERMEDIATE 26

[4-[(6-Bromo-3-hexynyl)oxy]butyl]benzene (i) 6-(4-Penylbutoxy)-3-hexyn-1-ol

Bromoethane (3.82 g) in THF (20 ml) was added dropwise to magnesium (0.85 g) under nitrogen at a rate to maintain gentle reflux. Intermediate 1 (7.0 g) in THF (10 ml) was added dropwise to the cloudy solution and the mixture was heated at 50°–60° for 1 h. Ethylene oxide (3.52 g) was added to the solution at 0° and the mixture was stirred at 0° for 10 min, at room temperature for 1 h, and at reflux for 3 h, treated with saturated aqueous ammonium chloride(100 ml) and extracted with ER (2×100 ml). The dried (MgSO4) extract was evaporated and the residue was purified by FCC eluting with CX-ER (20:7) to give a colourless oil (4.8 g). Distillation gave the title compound as a colourless oil (4.0 g) b.p. 165°–170°/0.3 mm Hg T.l.c. (CX-ER 1:1) RF 0.35

(ii) [4-[(6-Bromo-3-hexynyl)oxy]butyl]benzene

Triphenylphosphine (4.5 g) in dry MC (20 ml) was added dropwise to the product of stage (i) (3.8 g) and carbon tetrabromide (5.8 g) in dry MC (50 ml) at 0°. The solution was stirred at 0° for 1 h and MC was evaporated. The residue was treated with ER (100 ml), filtered and the filtrate was evaporated. The residue was purified by FCC eluting with CX followed by CX-ER (4:1) to give the title compound as a colourless oil (4.2 g). T.l.c. (CX-ER 9:1) Rf 0.4.

INTERMEDIATE 27

1-[4-[(5-Bromopentyl)oxy]-1-butynyl]-4-(3-methoxy-1-propynyl)benzene

CuI (19 mg) was added to a stirred solution of Intermediate 23 (2.72 g), Intermediate 7 (2.19 g), and BTPC (0.14 g) in a mixture of THF (15 ml) and DEA (15 ml). The mixture was stirred at room temperature under nitrogen for 18 h, the solvents evaporated at 50° in vacuo and the residual oil was partitioned between EA (100 ml) and 2N hydrochloric acid (100 ml). The organic layer was washed with further 2N hydrochloric acid (100 ml), dried and concentrated to afford a product which was purified by FCC eluting with ER-CX (1:9) providing the title compound as a dark red oil (3.16 g). T.l.c. (ER-H 1:8) Rf 0.30.

INTERMEDIATE 28

N-[[4-[4-[[6-[(Phenylmethyl)amino]hexyl]oxy]-1-butynyl]phenyl]methyl]pentanamide A mixture of Intermediate 22 (3.5 g), Intermediate 31 (2.85 g), BTPC (0.2 g), CuI (0.02 g), and diethylamine (50 ml) was stirred at room temperature under nitrogen for 18 h and evaporated. The residue was partitioned between aqueous sodium bicarbonate (1M; 50 ml) and EA (2×100 ml), and the dried organic phase was evaporated. The residue was purified by FCC eluting with EA to give the title compound as a yellow solid (2.3 g) m.p. 66°–67°.

INTERMEDIATE 29

(E)-4-[4-[(6-Bromohexyl)oxy]-1-butenyl]-2-methoxyphenol

A solution of Intermediate 8 (4.05 g) and 4-toluenesulphonic acid (2.34 g) in a mixture of THF (80 ml) and water (10 ml) was heated under reflux for 2.5 h and then the solvent evaporated in vacuo at 40° to yield a viscous oil. This was taken up in EA (100 ml) and the solution washed with 8% NaHCO3 solution (2×75 ml), dried, concentrated and purified by FCC eluting with EA-H (1:3) to give the title compound (3.60 g). T.l.c. (EA-CX 1:3) Rf 0.44.

INTERMEDIATE 30

4-[[3,5-Bis(phenylmethoxy)]phenyl]-3-buten-1-ol

A stirred suspension of [3-(1-methoxy-1-methylethoxy)propyl](triphenylphosphonium)bromide (4 g) in dry THF (25 ml) at 0° C. was heated with butyl lithium (5.28 ml) and the mixture stirred at 0° C. for 10 min. 3,5-Bis(phenylmethoxy)benzaldehyde (2.24 g) in dry THF (15 ml) was added and the mixture stirred for a further 45 min at room temperature under nitrogen, diluted with ER (100 ml) and filtered through silica (20 g) twice. The filtrate was evaporated in vacuo to give a yellow oil which was dissolved in a mixture of THF (50 ml), water (5 ml) and 2M hydrochloric acid (1 ml) and left at room temperature for 30 min. The mixture was basified with sodium bicarbonate solution and extracted with ER (200 ml). The organic phase was washed with water (150 ml), brine (100 ml), dried and evaporated in vacuo to give a yellow oil. Purification by FCC eluting with ER-CX (3:2) gave a colourless oil (1.48 g). T.l.c. (ER-CX 3:1) Rf 0.26

INTERMEDIATE 31

N-[6-[(3-Butynyl)oxy]hexyl]benzenemethanamine

Intermediate 5 (43.3 g) was added over 20 min to benzylamine (147 ml) at 120° under nitrogen. The reaction mixture was stirred at 120° for 2 h, the benzylamine was removed by distillation (70° ~0.1 torr) and ER (1 l) was added to the residue. The resultant precipitate was removed by filtration and the filtrate was concentrated to an oil which was purified by FCC eluting with CX-ER (2:1→ER) to give the title compound as a yellow oil (25.5 g). T.l.c. (EA-triethylamine 99:1) Rf 0.38.

INTERMEDIATE 32

(E)-4-[3-Methoxy-4-(methoxymethoxy)phenyl]-3-buten-1-ol n-Butyllithium (1.6M in hexane, 25 ml) was added dropwise to a stirred suspension of (3-hydroxypropyl)-triphenylphosphonium bromide (8.03 g) in dry THF (50 ml) cooled to 0° under nitrogen. The resulting blood-red solution was stirred at 0° for 10 min and then 3-methoxy-4-(methoxymethoxy)-benzaldehyde (3.60 g) in dry THF (10 ml) was added dropwise over 5 min. The mixture was allowed to warm to room temperature, stirred for 4 h, water (10 ml) was added and the majority of the solvent was removed in vacuo at 40°. A solution of the residual oil in ER (200 ml) was washed with water (150 ml), dried, treated with charcoal, concentrated and purified by FCC eluting with EA-H (1:1) to give the title compound (1.55 g). T.l.c. (EA-H 1:1) Rf 0.30.

INTERMEDIATE 33

7-[2-[4-Methylthio)phenyl]ethoxy]-2-heptanone (i) 1-[2-[(5-Bromopentyl)oxy]ethyl]-4-(methylthio)benzene 4-(methylthio)benzeneethanol (7.44 g) and 1,5 dibromopentane (30.48 g) were stirred rapidly at room temperature with TAB (1.0 g) and 12.5M aqueous sodium hydroxide (35 ml) for 64 h. The mixture was diluted with water (170 ml), extracted with ER (3×200 ml), and the combined organic extracts were washed consecutively with water (170 ml) and brine (170 ml), dried and evaporated. The residual oil (29.29 g) was purified by FCC eluting with ER-CX (0:100→3:97) to give the title compound as a colourless oil (10.68 g). T.l.c. (ER-CX 1:79) Rf 0.08.

(ii) 7-[2-[4-(Methylthio)phenyl]ethoxy]-2-heptanone

The product of stage (i) (5.00 g) in ER (7.0 ml) was added dropwise to magnesium turnings (0.384 g) with one crystal of iodine at room temperature under nitrogen with stirring. The stirred mixture was heated to reflux for 3 h under nitrogen and the solution of Grignard reagent was added slowly to a stirred solution of acetic anhydride (2.86 g) in ER (70 ml) over a period of 1 h maintaining the temperature between −60° and −70°. After a further 2 h at −60° to −70°, the reaction mixture was allowed to warm to −10° and treated with a saturated aqueous ammonium chloride solution (20 ml). The ER layer was separated and the aqueous phase was extracted with ER (3×40 ml). The combined extracts were washed with 2N sodium hydroxide (30 ml) and brine (30 ml). The washings were extracted with ER (3×40 ml) and these extracts, combined with the previous extracts were dried and evaporated. The residual oil (3.73 g) was purified by FCC eluting with ER-H (1:14→1:7) followed by ER-CX (1:7 to give the title compound (2.17 g).

Analysis Found: C, 69.9; H, 9.2; S, 11.05; $C_{16}H_{24}O_2S$ requires C, 68.55; H, 8.65; S, 11.45%

INTERMEDIATE 34

(4-(4-Morpholinyl)benzenebutanol

A mixture of 4-aminobenzenebutanol (7.5), 2-chloroethyl ether (6.5 g, 5.32 ml), DEA (11.74 g) and finely ground potassium iodide (15.0 g) was stirred in DMF (500 ml) at 100° under nitrogen for 65 h. The mixture was cooled, the solvent removed in vacuo at 55° and the residue partitioned between EA (250 ml) and water (100 ml). The aqueous layer was extracted with further EA (100 ml), the combined organic solutions washed with brine (150 ml), dried and evaporated onto FCC silica (15 g). The impregnated material was applied to an FCC column, elution with ER-CX (2:1) affording the title compound as a waxy cream solid (6.13 g) m.p. 51°-52°.

INTERMEDIATE 35

1,1-Dimethyl-5-[4-[4-(4-morpholinyl)phenyl]butoxy]-pentanamine (i) 2,2-Dimethyl-6-[4-[4-(4-morpholinyl)phenyl]butoxy]-hexanoic acid A solution of lithium diisopropylamide was prepared by treating diisopropylamine (5.32 g) in dry THF (20 ml) with n-butyllithium (1.53M in hexane: 34.4 ml) at −40° under nitrogen. The solution was stirred at 0° for 15 min, isobutyric acid (2.32 g) was added and the mixture stirred at room temperature for 3 h. Intermediate 9 (6.0 g) was added, the mixture stirred at room temperature for 20 h under nitrogen and then the solvents evaporated in vacuo at 40°. The viscous residue was triturated with water (250 ml), the pH adjusted to 6 by the addition of 2N hydrochloric acid and the mixture extracted with EA (2×200 ml). The organic layer was dried and concentrated in vacuo to afford the title compound as a pale brown oil (5.75 g). T.l.c. (ER) Rf 0.6.

(ii) (Phenylmethyl) 1,1-dimethyl-5-[4-[4-(4-morpholinyl)phenyl]butoxy]-pentylcarbamate Ethyl chloroformate (1.66 g) in acetone (5 ml) was added dropwise to a solution of the product of stage (i) (5.5 g) and triethylamine (2.13 ml) in acetone (50 ml) and water (5 ml) stirred at 0°. The mixture was stirred at 0° for 40 min and sodium azide (1 g) in water (10 ml) was added dropwise. The resulting suspension was stirred at room temperature for 45 min, diluted with water (100 ml) and extracted with T (2×100 ml). The dried extract was heated at 75°-80° for 2 h under nitrogen and evaporated in vacuo at 40°. The residual oil was dissolved in benzyl alcohol (10 ml) and the solution stirred at 70°-75° for 60 h under nitrogen and then the excess alcohol removed in vacuo at 95°. The resulting oil was purified by FCC eluting with ER-CX (1:2) to afford the title compound as a pale yellow oil (5.34 g). T.l.c. (ER-CX 1:2) Rf 0.23.

(iii) 1,1-Dimethyl-5-[4-[4-(4-morpholinyl)phenyl]butoxy]-pentanamine

A solution of the product of stage (ii) (4.60 g) in absolute ethanol (75 ml) was hydrogenated at room temperature and atmospheric pressure over a pre-reduced 10% palladium oxide on carbon catalyst (1 g, 50% paste in water) in absolute ethanol (25 ml). The catalyst was removed by filtration through 'hyflo' and the solvent evaporated in vacuo at 40° to yield the title compound as a colourless oil (3.0 g). T.l.c. (T-ET-A 39:10:1) Rf 0.32.

INTERMEDIATE 36

N-N-Dipropyl-4-[4-[[6-(phenylmethyl)amino]hexyl]oxy]-1-butynyl]benzamide

Copper (I) iodide (10 mg) was added to a stirred solution of Intermediate 21 (2 g), Intermediate 31 (1.57 g) and BTPC (70 mg) in diethylamine (30 ml) under nitrogen, and the mixture stirred under nitrogen overnight. The solution was evaporated in vacuo, the residue dissolved in MC (50 ml) and the solution evaporated onto FCC silica. Purification by FCC eluting with ER gave the title compound as an orange oil (1.2 g).

Analysis Found: C, 77.6; H, 9.4; N, 6.3. $C_{30}H_{42}N_2O_2$ requires C, 77.9; H, 9.2; N, 6.1%.

INTERMEDIATE 37

N-[4-[4-[[6-[[2-[3-[(Aminocarbonyl)amino]-4-(phenylmethoxy)phenyl]-2-oxoethyl](phenylmethyl)amino]hexyl]oxy]butyl]phenyl]butanesulphonamide N-[5-Bromoacetyl-2-[phenylmethoxy)phenyl]urea (0.96 g), Intermediate 10 (1.25 g) and DEA (0.68 g) in THF (50 ml) were stirred at room temperature under nitrogen for 20 h. The mixture was diluted with water (100 ml), extracted with EA (2×100 ml), dried and evaporated in vacuo to give an oil. Purification by FCC eluting with EA-CX (3:1) gave the title compound as a white foam (0.90 g). T.l.c. (EA-CX 3:1) Rf 0.27

INTERMEDIATE 38

(E)-N-[5-[2-[[6-[[4-(4-Hydroxy-3-methoxyphenyl)-3-butenyl]oxy]hexyl](phenylmethyl)amino]-1-oxoethyl]-2-(phenylmethoxy)phenyl]methane sulphonamide A solution of N-[5-bromoacetyl-2-(phenylmethoxy)phenyl]methanesulphonamide (0.6 g), Intermediate 11 (0.48 g) and DEA (0.39 g) in THF (10 ml) was left to stand for 48 hours. The precipitated DEA hydrobromide was filtered off and the filtrate evaporated in vacuo to give an oil. This was pre-absorbed onto FCC silica (5 g) and purified by FCC (80 g) eluting with CX-EA (3:2) providing the title compound as a yellow oil (0.38 g). T.l.c. (CX-EA 3:2) Rf 0.20

INTERMEDIATE 39

N-[5-[2-[[5-[4-[4-(3-Methoxypropyl)phenyl]butoxy]pentyl](phenylmethyl)amino]-1-oxoethyl]-2-(phenylmethoxy)phenyl]formamide A solution of N-[5-bromoacetyl-2-(phenylmethoxy)phenyl]formamide (0.70 g), Intermediate 12 (0.80 g) and DEA (0.52 g) in DMF (10 ml) was allowed to stand at room temperature for 3 h. The solvent was removed in vacuo at 55°, the residual oil was taken up in EA (50 ml) and the solution washed with water (50 ml). The aqueous phase was extracted with further EA (50 ml), the combined organic layers dried and concentrated to yield an orange oil which was purified by FCC eluting with EA-CX (1:2) to afford the title compound as colourless oil (0.89 g), T.l.c. (EA-H 1:1) Rf 0.45.

INTERMEDIATE 40

4-[4-[[6-[[2-[3-[[(Dimethylamino)sulphonyl]amino]-4-(phenylmethoxy)phenyl]-2-oxoethyl](phenylmethyl)amino]hexyl]oxy]-1-butynyl]-N,N-dipropyl benzamide as a yellow oil (0.47 g) t.l.c. (T-EA 5:1) Rf 0.289 was prepared from N'-5-[bromoacetyl-2-(phenylmethoxy)phenyl]-N,N-dimethylsulphamide (0.7 g), Intermediate 36 (0.76 g), and DEA (0.23 g) according to the method of Intermediate 39, except that the reaction mixture was stirred under nitrogen for 4 h, and T-EA (7:1) was used as eluant for the FCC purification.

INTERMEDIATE 41

(E)N-[2-Hydroxy-5-[1-hydroxy-2-[[6-[[4-[3,5-bis(-phenylmethoxy)phenyl]-3-butenyl]oxy]hexyl]amino]ethyl]phenyl]methanesulphonamide Intermediate 4 (2.13 g) was added dropwise to a stirred solution of Intermediate 43 (1.5 g) and DEA (0.57 g) in DMF (25 ml) at 70° under nitrogen. The solution was stirred at 70° for 6 h, diluted with water (100 ml), extracted with EA (2×100 ml), washed with water (100 ml), dried and evaporated in vacuo to give a brown oil. Purification by FCC eluting with EA-ME (9:2) gave the title compound as a brown oil (0.79 g). T.l.c. (T-ET-A 39:10:1) Rf 0.22

INTERMEDIATE 42

N-[5-[1-Hydroxy-2-[[1,1-dimethyl-5-[4-[4-(4-morpholinyl)phenyl]butoxy]pentyl]amino]ethyl]-2-(phenylmethoxy)phenyl]methanesulphonamide A mixture of N-[5-(oxoacetyl)-2-(phenylmethoxy)phenyl]methanesulphonamide hydrate (0.74 g) and Intermediate 35 (0.70 g) 2.0 mmol) in benzene (20 ml) was stirred and heated under reflux in a Dean-Stark apparatus for 0.5 h when water ceased to be collected. The solvent was removed in vacuo at 40°, the residual oil was dissolved in methanol (25 ml) and the solution stirred at 0° under nitrogen. Sodium borohydride (0.75 g) was added portionwise over 0.5 h, the mixture stirred at 0° for 15 min and then allowed to stand at room temperature for 20 h. The solution was acidified (pH 2) with 2N hydrochloric acid, the majority of the methanol evaporated in vacuo at 40° and the residual oil partitioned between EA (75 ml) and 8% sodium bicarbonate solution. The aqueous phase was extracted with further EA (50 ml), the combined organic solutions were dried and concentrated to yield a product which was purified by FCC eluting with T-ET-A (39:10:1) to yield the title compound as a pale brown viscous gum. T.l.c. (T-ET-A 39:10:1) Rf 0.42.

INTERMEDIATE 43 is N-[5-(2-amino-1-hydroxyethyl)-2-hydroxyphenyl]-methanesulphonamide.

INTERMEDIATE 44

N-(4-Iodobenzoyl)piperidine

4-Iodobenzoyl chloride (10.0 g) was added portionwise to piperidine (3.53 g) in triethylamine (40 ml) at 0° and the suspension was stirred at room temperature under nitrogen for 1 h. The reaction mixture was poured into 2N aqueous hydrochloric acid (200 ml) and extracted with EA (3×100 ml). The combined extracts were washed with water (100 ml), 8% aqueous sodium bicarbonate (100 ml) and water (10 ml), dried and concentrated. The resultant solid (10.25 g) was purified by FCC eluting with ER-H (1:2→1:1) to give the title compound as a white solid (9.33 g) m.p. 126°-127°.

INTERMEDIATE 45

N,N-Diethyl-4-iodobenzeneacetamide

4-Iodobenzeneacetyl chloride (10.62 g) was added portionwise to diethylamine (3.0 g) in triethylamine (40 ml) and washed in with MC (5 ml) at 0° under nitrogen and the suspension was stirred at room temperature for 2 h. ER (150 ml) was added, the mixture was filtered and the filtrate was concentrated to give a residue (7.94 g) which was purified by FCC eluting with ER-H (2:1) to give the title compound as a yellow oil (4.72 g). T.l.c. (ER) Rf 0.31.

INTERMEDIATE 46

1-Bromo-6-[(2-propynyl)oxy]hexane

A mixture of propargyl alcohol (5.6 g) 1,6-dibromohexane (73.2 g), TAB (0.5 g), and aqueous sodium hydroxide (50% w/v, 25 ml) was stirred at room temperature for 20 h, diluted with water (50 ml), and extracted with ER (2×100 ml). The dried extract was evaporated and the residue was purified by FCC eluting with CX followed by CX-ER (19:1) to give the title compound as a colourless oil (15.0 g). T.l.c. (CX-ER 9:1) Rf 0.4.

INTERMEDIATE 47

2-[4-[(6-Bromohexyl)oxy]butyl]-N,N-diethylbenzamide

A mixture of CuI (20 mg), 1-bromo-6-[(3-butynyl)oxy]hexane (3.04 g), N,N-diethyl-2-iodobenzamide (3.95 g), BTPC (200 mg), N,N-dicyclohexylamine (2.60 g) and acetonitrile (20 ml) was stirred under nitrogen at room temperature for 4.5 h, diluted with ether (200 ml) and filtered. The filtrate was evaporated in vacuo, the residue in ethanol (100 ml) was treated with charcoal and the solvent evaporated in vacuo. The residual oil (5.32 g) in absolute ethanol (190 ml) was hydrogenated over pre-reduced 10% PDO-C (50% paste in water, 1.25 g) in absolute ethanol (20 ml), filtered through hyflo and evaporated in vacuo to give an oil. Purification by FCC eluting with T-EA-triethylamine (95:5:1) followed by FCC eluting with CX-EA (2:1) gave the title compound as a yellow oil (2.04 g). T.l.c. (T-ET-A-40:10:1) Rf 0.14.

Similarly were prepared Intermediates 48–51

INTERMEDIATE 48

4-[4-[(5-Bromopentyl)oxy]butyl]-N,N-diethylbenzamide as a light brown oil (5.81 g), t.l.c. (ER) Rf 0.37, from CuI (25 mg), N,N-diethyl-4-iodobenzamide (6.06 g), Intermediate 2 (4.38 g), BTPC (250 mg) and dicyclohexylamine (4.0 g) in acetonitrile (30 ml), reaction time 2 h, followed by hydrogenation using 10% PD-C (50% aqueous paste) as catalyst. Purification of product was carried out using Merck 7734 silica, eluting with H-ER (1:1) and ER.

INTERMEDIATE 49

N-[4-[4-[(6-Bromohexyl)oxy]butyl]benzoyl]piperidine as a dark brown oil (7.55 g), t.l.c. (ER-H 2:1) Rf 0.25, from Intermediate 44 (9.30 g), 1-bromo-6-[(3-butynyl)oxy]hexane (6.46 g) N,N-dicyclohexylamine (5.90 g), BTPC (150 mg) and CUI (30 mg) in acetonitrile (90 ml), reaction time 20 h. 10% PD-C was used as catalyst for hydrogenation, and ER-H (2:1) and CF as eluents for FCC purification

INTERMEDIATE 50

4-[4-[(6-Bromohexyl)oxy]butyl]-N,N-diethylbenzeneacetamide as a dark brown oil (3.51 g), t.l.c. (ER-H 2:1) Rf 0.18, from Intermediate 45 (4.65 g) 1-bromo-6-[(3-butynyl)oxy]hexane (3.22 g), N,N-dicyclohexylamine (2.94 g), BTPC (75 mg) and CuI (15 mg) in acetonitrile (30 ml), with reaction time, hydrogenation catalyst and FCC purification as in Intermediate 49.

INTERMEDIATE 51

3-[4-[(6-Bromohexyl)oxy]butyl]-N,N-diethylbenzamide as a brown oil (5.91 g), t.l.c. (H-ER 1:1) Rf 0.175, from N,N-diethyl-3-iodobenzamide (8.49 g) 1-bromo-6-[(3-butynyl)oxy]hexane (6.99 g), BTPC (350 mg), CuI (250 mg) and dicyclohexylamine (6.45 g) in acetonitrile (35 ml). After stirring at room temperature for 2 days, the solvent was evaporated and the residue partitioned between water (100 ml) and EA (100 ml). The phases were separated, charcoal (5 g) was added to the organic layer which was then dried and concentrated to an oil. Ethanol (100 ml) was added to the oil, the resulting fine brown precipitate was removed by filtration and the filtrate was hydrogenated using 10% PD-C as a catalyst. ER-CX (1:2) was used as eluent for FCC purification.

INTERMEDIATE 52

4-[3-[[6-[(Phenylmethyl)amino]hexyl]oxy]propyl]-N,N-dipropylbenzamide

A suspension of Intermediate 21 (6.62 g), Intermediate 46 (4.40 g), dicyclohexylamine (4.0 g), BTPC (250 mg) and CuI (25 mg) in acetonitrile (40 ml) was treated as in Intermediate 25, followed by hydrogenation using pre-reduced 10% PD-C as catalyst, with FCC purification using H-ER (2:1) as eluent. The resultant orange oil (5.1 g) was added to benzylamine (15 ml) at 140° under nitrogen. After 2 h the reaction mixture was added to 2N hydrochloric acid (200 ml) and ice (100 ml). The aqueous mixture was extracted with EA (3×100 ml) and the combined organic extracts were washed with 2N sodium carbonate (2×100 ml), water and brine, dried and concentrated to a dark oil which was purified by FCC eluting with T-ER-triethylamine (95:5:1→90:10:1) to give the title compound as a pale yellow oil (2.4 g) t.l.c. T-ET-triethylamine (90:10:1) Rf 0.36.

INTERMEDIATE 53

N-[6-[2-[4-(N,N-Dimethylamino)phenyl]ethoxy]hexyl]-benzenemethanamine

A mixture of 1,6-dibromohexane (73.84 g) 4-(N,N-dimethylamino)benzeneethanol (10 g), 50% w/v sodium hydroxide solution (200 ml) and TAB (3.4 g) was vigorously stirred at room temperature for 72 h, diluted with water (500 ml) and extracted with ER (2×100 ml). The dried extracts were evaporated to give a yellow oil which was purified by FCC eluting with H then H-EA (9:1) to give 4-[2-[(6-bromohexyl)oxy]ethyl]-N,N-dimethylbenzeneamine as a yellow oil. The benzeneamine (15 g) was added to benzylamine (45 ml) with stirring at 140° under nitrogen and stirring continued for 2 h. The benzylamine was removed in vacuo at 90°, the solution was partitioned between sodium bicarbonate (150 ml) and EA (2×100 ml) and the combined organic layers dried and concentrated to give a product which was purified by FCC eluting with ER-H (1:1→ER) to give the title compound as a yellow oil (11.1 g) t.l.c. (T-ET-A 95:4:1) Rf 0.62.

EXAMPLE 1

(a)

N,N-Diethyl-4-[4-[[6-[[2-hydroxy-2-[4-hydroxy-3-[(methylsulphonyl)amino]phenyl]ethyl]amino]hexyl]oxy]butyl]benzamide, benzoate (salt)

Intermediate 17 (1.0 g) in DMF (2 ml) was added dropwise to a solution of Intermediate 43 (1.2 g) and DEA (1.3 g) in DMF (20 ml) at 75°. The solution was heated at 75°–80° for 90 min and evaporated under reduced pressure. The residue was purified by FCC eluting with T-ET-A (80:20:1) to give a colourless gum. The gum in CF (10 ml) was treated with benzoic acid (0.3 g) in CF (5 ml) and CF was evaporated. The residue was triturated with ER (2×25 ml) to give the title compound as a white solid (0.55 g) m.p. 90°-92°.

Analysis Found: C, 63.3; H, 7.55; N, 5.9 $C_{29}H_{48}N_3O_6S.C_7H_6O_2$ requires C, 62.8; H, 7.9; N, 6.1%

Similarly prepared were:

(b) Propyl 4-[4-[[5-[[2-hydroxy-2-[4-hydroxy-3-[(methylsulphonyl)amino]phenyl]ethyl]amino]pentyl]oxy]-1-butynyl]benzoate as a white solid (0.26 g) m.p. 88°-90°.

Analysis Found: C, 61.0; H, 7.0; N, 5.0. $C_{28}H_{38}N_2O_7S$ requires C, 61.5; H, 7.0; N, 5.1%.

From Intermediate 43 (10 g), Intermediate 15 (1.43 g) and DEA (1.0 g) after a reaction time of 2 h, and omitting treatment with benzoic acid in CF.

(c) N-[2-Hydroxy-5-[1-hydroxy-2-[[6-[4-[4-(methylthio)phenyl]butoxy]hexyl]amio]ethyl]phenyl]methanesulphonamide as a beige solid (0.3 g) m.p. 92°-93°.

Analysis Found: C, 59.0; H, 7.9; N, 5.4. $C_{26}H_{40}N_2O_5S_2.2H_2O$ requires C, 59.1; H, 8.4; N, 5.3%.

From Intermediate 43 (0.8 g), Intermediate 6 (1.3 g) and DEA (1.0 g) after a reaction time of 3 h, and omitting treatment with benzoic acid in CF.

(d) N-[2-Hydroxy-5-[1-hydroxy-2-[[6-[4-(4-nitrophenyl)butoxy]hexyl]amino]ethyl]phenyl]methanesulphonamide as a beige solid (1.15 g) m.p. 77°-80°.

Analysis Found: C, 57.0; H, 7.1; N, 7.85. $C_{25}H_{37}N_3O_7S$ requires C, 57.3; H, 7.1; N, 8.0%.

From Intermediate 43 (2.5 g), Intermediate 3 (3.6 g) and DEA (2.6 g) after a reaction time of 2 h, and omitting treatment with benzoic acid in CF.

EXAMPLE 2

(a) (E)-N-[2-Hydroxy-5-[1-hydroxy-2-[[6-[[4-(4-fluorophenyl)-3-butenyl]oxy]hexyl]amino]ethyl]phenyl]methanesulphonamide Intermediate 2 (1.34 g) was added to a stirred solution of Intermediate 43 (1.50 g) and DEA (0.57 g) in DMF (25 ml) at 70° under nitrogen. The solution was stirred at 70° for 5 h, diluted with water (100 ml) and extracted with EA (2×100 ml). The organic phase was washed with water (100 ml), dried and evaporated in vacuo to give a brown oil which was purified by FCC eluting with EA-ME (9:1) to give a brown foam. Trituration with ER gave the title compound as a white solid (0.47 g) m.p. 79°-80°.

Analysis Found: C, 59.6; H, 7.15; N, 5.6. $C_{25}H_{35}FN_2O_5S.0.5H_2O$ requires C, 59.6; H, 7.2; N, 5.6%.

Similarly prepared was:

(b) N-[2-Hydroxy-5-[1-hydroxy-2-[[6-(4-phenylbutoxy)-3-hexynyl]amino]ethyl]phenyl]methanesulphonamide as a yellow foam (159 mg). T.l.c. (T-ET-A, 39:10:1) Rf 0.22

Analysis Found: C, 61.6; H, 7.3; N, 5.7. $C_{25}H_{34}N_2O_5.0.5H_2O$ requires C, 62.1; H, 7.3; N, 5.8%.

From Intermediate 43 (0.8 g), Intermediate 26 (1 g) and DEA (0.45 g) after a reaction time of 2 h.

EXAMPLE 3

(a) Propyl 4-[4-[[5-[[2-hydroxy-2-[4-hydroxy-3-[(methylsulphonyl)amino]phenyl]ethyl]amino]pentyl]oxy]butyl]benzoate A solution of Example 1(b) (0.2 g) in ET (20 ml) was hyrogenated over 10% PD-C (0.05 g), filtered through hyflo and evaporated. The residue was triturated with ER (20 ml) to give the title compound as an off-white solid (0.19 g) m.p. 74°-76°.

Analysis Found: C, 60.6; H, 7.4; N, 5.0. $C_{28}H_{42}N_2O_7S$ requires C, 61.1; H, 7.7; N, 5.1%.

Similarly prepared were:

(b) N-[2-Hydroxy-5-[1-hydroxy-2-[[6-[4-(3,5-dihydroxyphenyl)butoxy]hexyl]amino]ethyl]phenyl]methanesulphonamide as a beige solid (0.27 g) m.p. 73°-74° (dec)

Analysis Found: C, 56.3; H, 7.6; N, 5.2. $C_{25}H_{38}N_2O_7S.1H_2O$ requires C, 56.8; H, 7.6; H, 5.3%.

From Intermediate 41 (0.5 g), pre-reduced 10% PD-C (40 mg) and 5% PT-C (30 mg).

(c) N-[4-[4-[[6-[[2-[3-[(Aminocarbonyl)amino]-4-hydroxyphenyl]ethyl]amino]hexyl]oxy]butyl]phenyl]butanesulphonamide as a beige foam (0.45 g). T.l.c. (T-ET-A 39:10:1) Rf 0.16

Analysis Found: C, 58.3; H, 7.75; N, 8.9. $C_{29}H_{46}N_4O_6S.H_2O$ requires C, 58.4; H, 8.1; N, 9.4%.

From Intermediate 37 (0.8 g), pre-reduced 10% PD-C (200 mg) and 5% PT-C (200 mg).

(d) N-[5-[2-[[6-[4-(4-Aminophenyl)butoxy]hexyl]amino]-1-hydroxyethyl]-2-hydroxyphenyl]methanesulphonamide as a beige solid (0.3 g) m.p. 57°-60°

Analysis Found: C, 58.3; H, 7.5; N, 8.0. $C_{25}H_{39}N_3O_5S.H_2O$ requires C, 58.7; H, 8.0; N, 8.2%.

From Example 1(d) (0.5 g), 10% PD-C (0.1 g) and 5% PT-C (0,1 g)

EXAMPLE 4

N-[2-Hydroxy-5-[1-hydroxy-2-[[5-[4-[4-(3-methoxypropyl)phenyl]butoxy]pentyl]amino]ethyl]phenyl]formamide, benzoate (salt)

A solution of Intermediate 39 (0.85 g) in absolute ET (25 ml) was hydrogenated over pre-reduced 10% PDO-C (0.5 g) and 5% PTO-C (0.25 g). The mixture was filtered through hyflo and the solvent removed to yeild an oil which was purified by FCC eluting with T-ET-A (39:10:1) to give the title compound free base as a viscous colourless oil (0.2 g). This was dissolved in ME (5 ml), benzoic acid (50 mg) was added and the solvent evaporated to give a viscous oil which on trituration with ER gave the title compound as a white powder (0.16 g) m.p. 88°-91°

Analysis Found: C, 68.21; H, 7.75; N, 4.54; $C_{28}H_{42}N_2O_5.C_7H_6O_2.0.5H_2O$ requires C, 68.04; H, 7.99; N, 4.53%

EXAMPLE 5

N-[2-Hydroxy-5-[1-hydroxy-2-[[6-[4-(4-hydroxy-3-methoxyphenyl)butoxy]hexyl]amino]ethyl]phenyl]methanesulphonamide A solution of Intermediate 38 (0.36 g) in absolute ethanol (20 ml) was hydrogenated over pre-reduced 10% PD-C (40 mg) and 5% PT-C (40 mg) in absolute ET (5 ml). The mixture was filtered through hyflo and evaporated to give a brown oil. Purification by FCC eluting with T-ET-A (39:10:1) gave a brown oil which on trituration with ER gave the title compound as a brown foam (40 mg) T.l.c. (T-ET-A 39:10:1) Rf 0.23.

Analysis Found: C, 58.4; H, 7.85; N, 4.9. $C_{26}H_{40}N_2O_7S.0.5H_2O$ requires C, 58.5; H, 7.7; N, 5.25%.

EXAMPLE 6

N-[[4-[4-[[6-[[2-Hydroxy-2-[4-hydroxy-3-[(methylsulphonyl)amino]phenyl]ethyl]amino]hexyl]oxy]butyl]phenyl]methyl]pentanamide, benzoate (salt)

A solution of N-[5-(bromoacetyl)-2-(phenylmethoxy)phenyl]methanesulphonamide (0.9 g), Intermediate 28 (1.0 g) and DEA (0.65 g) in THF (15 ml) was left at room temperature for 20 h, filtered, and evaporated. The residue was purified by FCC eluting with ER to give a yellow oil. The oil in ET (40 ml) was hydrogenated over 10% PD-C (0.3 g) and 5% PT-C (0.2 g), filtered and evaporated. The residue was purified by FCC eluting with T-ET-A (80:20:1) to give a colourless gum. A solution of the gum (0.2 g) in CF (15 ml) was treated with benzoic acid (0.7 g) and evaporated. The residue was triturated with ER (15 ml) to give the title compound as a white solid (0.2 g) m.p. 88°–89°

Analysis Found: C, 63.0; H, 7.7; N, 5.8. $C_{31}H_{49}N_3O_6S.C_7H_8O_2$ requires C, 63.1; H, 7.8; N, 5.8%.

EXAMPLE 7

4-[4-[[6-[[2-[3-[[(Dimethylamino)sulphonyl]amino]-4-hydroxyphenyl]-2-hydroxyethyl]amino]hexyl]oxy]butyl]-N,N-dipropylbenzamide, (E)-2-butenedioate (salt) (1:1)

A solution of Intermediate 40 (0.43 g) in absolute ET (30 ml) was hydrogenated over a mixture of pre-reduced 5% PTO-C (100 mg) and 10% PDO-C (100 g) in absolute ET (10 ml). The mixture was filtered through 'hyflo' and evaporated in vacuo to give a yellow oil (0.27 g). Purification by FCC eluting with T-ET-A (39:10:1) gave a yellow oil (200 mg) which was dissolved in methanol (2 ml) and treated with fumaric acid (40 mg). The solution was evaporated in vacuo and the residue triturated with ER to give the title compound as a cream foam (0.2 g). T.l.c. (T-ET-A 39:10:1) Rf 0.21.

Analysis Found: C, 58.6; H, 8.0; N, 6.9. $C_{33}H_{54}N_4O_6S.C_4H_2O_4.0.2H_2O$ requires C, 58.9; H, 7.8; N, 7.4%.

EXAMPLE 8

N-[2-Hydroxy-5-[1-hydroxy-2-[[1,1-dimethyl-5-[4-[4-(4-morpholinyl)phenyl]butoxy]pentyl]amino]ethyl]phenyl]methanesulphonamide A solution of Intermediate 42 (0.65 g) in absolute ethanol (25 ml) was hydrogenated at atmospheric pressure and room temperature over pre-reduced 10% PDO-C (0.5 g, 50% paste in H₂O). The catalyst was removed by filtration through 'hyflo'. Purification by FCC eluting with T-ET-A (38:10:1) afforded the title compound as a fawn powder (128 mg) m.p. 165°–167°.

Analysis Found: C, 62.22; H, 8.37; N, 6.99. $C_{30}H_{47}N_3O_6S$ requires C, 62.36; H, 8.20; N, 7.27%.

EXAMPLE 9

N-[2-Hydroxy-5-[1-hydroxy-2-[[1-methyl-6-[2-[4-(methylthio)phenyl]ethoxy]hexyl]amino]ethyl]phenyl]methanesulphonamide A solution of Intermediate 43 (0.62 g), Intermediate 33 (0.7 g) and acetic acid (0.18 g) in methanol (15 ml) was treated with sodium cyanoborohydride (0.19 g) under nitrogen and left at room temperature for 18 h in the presence of molecular sieves (4 A). Aqueous sodium bicarbonate (1M; 50 ml) was added and the mixture was extracted with EA (2×100 ml). The dried extract was evaporated and the residue was purified by FCC eluting with T-ET-A (80:20:1) to give a semi-solid residue which was triturated with ER (50 ml) to give the title compound as a white solid (0.45 g) m.p. 133°–138°.

Analysis Found: C, 58.8; H, 7.6; N, 5.3. $C_{25}H_{38}N_2O_5S_2$ requires C, 58.8; H, 7.5; N, 5.5%.

EXAMPLE 10

N,N-Dipropyl-4-[3-[[6-[[2-hydroxy-2-[4-hydroxy-3-[(methylsulphonyl)amino]phenyl]ethyl]amino]hexyl]oxy]propyl]benzamide, benzoate (salt)

A solution of N-[5-(bromoacetyl)-2-(phenylmethoxy)phenyl]methanesulphonamide (1.93 g), Intermediate 52 (2.10 g), and DEA (0.68 g) in dichloromethane (45 ml) was stirred under nitrogen for 24 h. The mixture was diluted with water (150 ml), extracted with ether (200 ml) and the organic phase washed with brine (50 ml), dried and evaporated in vacuo. A solution of the resultant yellow oil (3.57 g) in absolute ethanol (170 ml) was hydrogenated over a mixture of pre-reduced 10% PDO-C (1.0 g) and 5% PTO-C (1.2 g) catalysts in absolute ethanol (20 ml), filtered through hyflo and evaporated in vacuo to give an oil. Purification by FCC eluting with T-ET-A (40:20:1) gave an oil which on trituration with ER gave the free base of the title compound as a white foam (1.40 g), t.l.c. (T-ET-A 40:10:1) Rf 0.16. A portion (0.60 g) was dissolved in methanol (10 ml) and treated with benzoic acid (0.14 g) to give the title compound as a white solid (0.54 g) m.p. 100.5°–101.5°.

Analysis Found: C, 62.2; H, 7.8; N, 5.7. $C_{31}H_{49}N_3O_6S.C_7H_6O_2.H_2O$ requires C, 62.3; H, 7.8; N, 5.7%.

EXAMPLE 11

N-[2-Hydroxy-5-[1-hydroxy-2-[[6-[2-[4-(dimethylamino)phenyl]ethoxy]hexyl]amino]ethyl]phenyl]methane sulphonamide The title compound was prepared as a light brown solid (450 mg) m.p. 45°–50°

Analysis Found: C, 59.27; H, 8.05; N, 8.18; $C_{25}H_{39}N_3O_5S.0.7H_2O$ requires C, 59.31; H, 8.04; N, 8.29; S, 6.33.

From N-[5-(bromoacetyl)-2-(phenylmethoxy)phenyl]methane sulphonamide (4 g), Intermediate 53 (3.54 g) and DEA (2.1 g) according to the method of Example 10, except that 10% PD-C (1.5 g) and 5% PT-C (1.5 g) was used as the hydrogenation catalyst, T-ET-A (80:20:1) was used as the eluant for FCC, and treatment with benzoic acid has omitted.

Examples 12–16 were prepared according to the method of Example 1(a):

EXAMPLE 12

N,N-Diethyl-4-[4-[[5-[[2-hydroxy-2-[4-hydroxy-3-[(methylsulphonylamino]phenyl]ethyl]amino]pentyl]oxy]butyl]benzamide, benzoate salt, as a solid (1.35 g) m.p. 92°–105°, t.l.c. (T-ET-A 38:10:2) Rf 0.19.

Analysis Found: C, 61.88; H, 7.58; N, 5.99%. $C_{29}H_{45}N_3O_6.0.8C_7H_6O_2.0.5H_2O$ requires C, 61.98; H, 7.64; N, 6.27%.

From Intermediate 43 (2.5 g), DEA (0.89 g) and Intermediate 48 (2.7 g), after a reaction time of 3–4 h. T-ET-A (78:20:2 then 73:25:2) was used as eluent for FCC, and methanol as the solvent for treatment with benoic acid (0.45 g).

EXAMPLE 13

N-[2-Hydroxy-5-[1-hydroxy-2-[[6-[4-[4-(1-piperidinylcarbonyl)phenyl]butoxy]hexyl]amino]ethyl]phenyl]methanesulphonamide hydrobromide From Intermediate 43 (1.0 g), Intermediate 49 (1.15 g) and DEA (0.38 g), after a reaction time of 4 h. T-ET-A (80:20:2) was used as eluent for FCC, and the resulting foam (0.28 g) in methanol (2 ml) was treated with hydrogen bromide in methanol (1M, 0.4 ml). The solution was concentrated and the residue triturated with ER to give the title compound as a yellow foam (0.22 g) t.l.c. (T-ET-A 80:20:2) Rf 0.16.

Analysis Found: C, 53.3; H, 7.0; N, 5.7; S, 4.6; Br, 12.0. $C_{31}H_{47}N_3O_6S.HBr.1.5H_2O$ requires C, 53.4; H, 7.2; N, 6.0; S, 4.6; Br, 11.5%.

EXAMPLE 14

N,N-Diethyl-2-[4-[[6-[[2-hydroxy-2-[4-hydroxy-3-[(methylsulphonyl)amino]phenyl]ethyl]amino]hexyl]oxy]butyl]benzamide acetate (salt)

From Intermediate 43 (1.70 g), Intermediate 47 (1.9 g) and DEA (0.66 g). After a reaction time of 3 h the solvent was evaporated to vacuo and the residue dissolved in methanol (30 ml) and pre-absorbed onto FCC silica. Purification by FCC eluting with T-ET-A (40:10:1) gave a foam (0.56 g). This was dissolved in methanol (10 ml) and treated with glacial acetic acid (0.06 ml) to give the title compound as a buff foam (0.40 g), t.l.c. (T-ET-A 40:10:1) Rf 0.09.

Analysis Found: C, 58.5; H, 7.5; N, 6.0. $C_{30}H_{47}N_3O_6S.C_2H_4O_2.H_2O$ requires C, 58.6; H, 8.1; N, 6.4%.

EXAMPLE 15

N,N-Diethyl-4-[4-[[6-[[2-[4-hydroxy-3-[(methylsulphonyl)amino]phenyl]ethyl]amino]hexyl]oxy]butyl]benzene acetamide, benzoate (salt)

as a cream solid (80 mg) m.p. 114°–116°.

Analysis Found: C, 62.7; H, 7.7; N, 5.5; S, $C_{31}H_{49}N_3O_6S.1.25C_7H_6O_2.H_2O$ requires C, 62.6; H, 7.7; N, 5.5; S, 4.2%.

From Intermediate 43 (2.0 g), Intermediate 50 (229 g) and DEA (0.76 g), after a reaction time of 3 h. Following FCC, the resulting foam (0.7 g) was partitioned between EA (50 ml) and 8% aqueous sodium bicarbonate (50 ml), and the dried organic layer concentrated to give a foam (0.20 g) which was then treated with benzoic acid (80 mg) in chloroform.

EXAMPLE 16

N,N-Diethyl-3-[4-[[6-[[2-hydroxy-2-[4-hydroxy-3-[(methyl sulphonyl)amino)phenyl]ethyl]amino]hexyl]oxy]butyl)benzamide, as a sticky pink foam (1.2 g), t.l.c. (T-ET-A 80:20:2) Rf 0.1.

Analysis Found C, 62.27; H, 8.25; N, 7.03; S, 5.61. $C_{30}H_{47}N_3O_6S$ requires: C, 62.36; H, 8.20; N, 7.27; O, 5.55%

From Intermediate 51 (3.0 g), Intermediate 43 (2.9 g) and DEA (3.6 g), at a reaction temperature of 100°, and using T-ET-A (80:20:2)→T-methanol-A (50:50:2) as the FCC eluent.

The following are examples of suitable pharmaceutical compositions according to the invention. The term "active ingredient" is used herein to refer to a compound of the invention.

Tablets (Direct Compression)

|  | mg/tablet |
|---|---|
| Active ingredient | 2.0 |
| Microcrystalline Cellulose USP | 196.5 |
| Magnesium Stearate BP | 1.5 |
| Compression weight | 200.0 |

The active ingredient is sieved through a suitable sieve, blended with the excipients and compressed using 7 mm diameter punches.

Tablets of other strengths may be prepared by altering the ratio of active ingredient to microcrystalline cellulose or the compression weight and using punches to suit.

The tablets may be film coated with suitable film forming materials, such as hydroxypropylmethylcellulose, using standard techniques. Alternatively the tablets may be sugar coated.

Syrup (Sucrose-free)

|  | mg/5 ml dose |
|---|---|
| Active ingredient | 2.0 mg |
| Hydroxypropyl methylcellulose USP (viscosity type 4000) | 22.5 mg |
| Buffer | |
| Flavour | |
| Colour | as required |
| Preservative | |
| Sweetener | |
| Purified Water BP to | 5.0 ml |

The hydroxypropyl methylcellulose is dispersed in hot water, cooled and then mixed with an aqueous solution containing the active ingredient and the other components of the formulation. The resultant solution is adjusted to volume and mixed. The syrup is clarified by filtration.

Metered Dose Pressurised Aerosol

A. Suspension Aerosol

|  | mg/metered dose | Per can |
|---|---|---|
| Active ingredient micronised | 0.100 | 26.40 mg |

33
-continued

|  | mg/metered dose | Per can |
| --- | --- | --- |
| Oleic Acid BP | 0.100 | 2.64 mg |
| Trichlorofluoromethane BP | 23.64 | 5.67 g |
| Dichlorodifluoromethane BP | 61.25 | 14.70 g |

The active ingredient is micronised in a fluid energy mill to a fine particle size range. The Oleic Acid is mixed with the Trichlorofluoromethane at a temperature of 10°–15° C. and the micronised drug is mixed into the solution with a high shear mixer. The suspension is metered into aluminium aerosol cans and suitable metering valves delivering 85 mg of suspension are crimped onto the cans and the Dichlorodifluoromethane is pressure filled into the cans through the valves.

B. Solution Aerosol

|  | mg/metered dose | Per can |
| --- | --- | --- |
| Active ingredient | 0.055 | 13.20 mg |
| Ethanol BP | 11.100 | 2.66 g |
| Dichlorotetrafluoroethane BP | 25.160 | 6.04 g |
| Dichlorodifluoromethane BP | 37.740 | 9.06 g |

Oleic acid BP, or a suitable surfactant e.g. Span 85 (sorbitan trioleate) may also be included.

The active ingredient is dissolved in the ethanol together with the oleic acid or surfactant if used. The alcoholic solution is metered into suitable aerosol containers followed by the dichlorotetrafluoroethane. Suitable metering valves are crimped onto the containers and dichlorodifluoromethane is pressure filled into them through the valves.

Injection for Intravenous Administration

|  | mg/ml |
| --- | --- |
| Active ingredient | 0.5 mg |
| Sodium Chloride BP | as required |
| Water for Injection BP to | 1.0 ml |

Sodium chloride may be added to adjust the tonicity of the solution and the pH may be adjusted, using acid or alkali, to that of optimum stability and/or facilitate solution of the active ingredient. Alternatively suitable buffer salts may be used.

The solution is prepared, clarified and filled into appropriate size ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen or other suitable gas.

Inhalation Cartridges

|  | mg/cartridge |
| --- | --- |
| Active ingredient micronised | 0.200 |
| Lactose BP to | 25.0 |

The active ingredient is micronised in a fluid energy mill to a fine particle size range prior to blending with normal tabletting grade lactose in a high energy mixer. The powder blend is filled into No. 3 hard gelatin capsules on a suitable encapsulating machine. The contents of the cartridges are administered using a powder inhaler such as the Glaxo Rotahaler.

We claim:

1. A compound of formula (I)

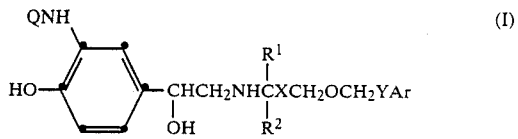

wherein

Ar represents a phenyl group optionally substituted by one or more substituents selected from halogen atoms, or the groups $C_{1-6}$ alkyl, $C_{1-6}$ alkoxy, nitro, $-(CH_2)_qR$, $-(CH_2)_rR^{10}$ or $-O(CH_2)_tR^{11}$, or Ar is a phenyl group substituted by an alkylenedioxy group of formula $-O(CH_2)_pO-$;

where R is hydroxy, $-NR^3R^4$, $-NR^5COR^6$, $-NR^5SO_2R^7$, $-COR^8$, $-SR^9$, $-SOR^9$, $SO_2R^9$ or $-CN$;

$R^1$ and $R^2$ each represent a hydrogen atom or a $C_{1-3}$ alkyl group with the proviso that the sum total of carbon atoms in $R^1$ and $R^2$ is not more than 4;

$R^3$ and $R^4$ each represents a hydrogen atom or a $C_{1-4}$ alkyl group or $-NR^3R^4$ forms a saturated heterocyclic amino group which has 5–7 ring members and optionally contains in the ring one or more atoms selected from $-O-$ or $-S-$ or a group $-NH-$ or $-N(CH_3)-$;

$R^5$ represents a hydrogen atom or a $C_{1-4}$ alkyl group;

$R^6$ represents a hydrogen atom or a $C_{1-4}$ alkyl, $C_{1-4}$ alkoxy, phenyl or $-NR^3R^4$ group;

$R^7$ represents a $C_{1-4}$ alkyl, phenyl or $-NR^3R^4$ group;

$R^8$ represents hydroxy, $C_{1-4}$ alkoxy or $-NR^3R^4$;

$R^9$ is a hydrogen atom or a $C_{1-4}$ alkyl or phenyl group;

$R^{10}$ is a $C_{1-4}$ alkoxy group;

$R^{11}$ represents a hydroxy or $C_{1-4}$ alkoxy group;

p represents 1 or 2;

q represents an integer from 0 to 3;

r represents an integer from 1 to 3;

t is 2 or 3;

X represents a $C_{1-7}$ alkylene, $C_{2-7}$ alkenylene or $C_{2-7}$ alkynylene chain;

Y represents a bond, or a $C_{1-6}$ alkylene, $C_{2-6}$ alkenylene or $C_{2-6}$ alkynylene chain with the proviso that the sum total of carbon atoms in X and Y is 2 to 10;

Q represents a group $R^{12}CO-$, $R^{12}NHCO$, $R^{12}R^{13}NSO_2-$, or $R^{14}SO_2$ where $R^{12}$ and $R^{13}$ each represent a hydrogen atom or a $C_{1-3}$ alkyl group, and $R^{14}$ represents a $C_{1-4}$ alkyl group; with the proviso that when X represents $C_{1-7}$ alkylene, and Y represents a bond or $C_{1-6}$ alkylene, then the group Ar does not represent an unsubstituted phenyl group or a phenyl group substituted by one or more substituents selected solely from halogen atoms or $C_{1-6}$ alkyl or $C_{1-6}$ alkoxy groups or an alkylenedioxy group $-O(CH_2)_pO$; or a physiologically acceptable salt or solvate thereof.

2. A compound according to claim 1 in which $-X-$ is $-(CH_2)_2-$, $-(CH_2)_3-$, $-(CH_2)_4-$, $-(CH_2)_5-$, $-CH_2C\equiv C-$, $-(CH_2)_2CH=CH-$, $-(CH_2)_2C\equiv C$, $-CH=CHCH_2-$, $-CH=CH(CH_2)_2-$ or $-CH_2C\equiv CCH_2-$ and $-Y-$ is $-CH_2-$, $-(CH_2)_2-$, $-(CH_2)_3-$, $-(CH_2)_4-$, $-(CH_2)_5-$, $-(CH_2)_6-$, $-CH=CH-$, $-C\equiv C-$, $-CH_2CH=CH-$, or $-CH_2C\equiv C-$.

3. A compound according to claim 1 in which $R^1$ and $R^2$ independently represent a hydrogen atom or a methyl group.

4. A compound according to claim 1 in which Q is HCO—, $CH_3CO$—, $NH_2CO$—, $(CH_3)_2NSO_2$— or $CH_3SO_2$—.

5. A compound according to claim 4 in which Q is $CH_3SO_2$—.

6. A compound according to claim 1 in which

Ar is phenyl; or Ar is phenyl substituted by one or more substituents selected from chlorine, bromine, iodine, fluorine, methyl, ethyl, methoxy, ethoxy, $-(CH_2)_qR$, $-NO_2$, $-CH_2OCH_3$, $-(CH_2)_3OCH_3$, $-O(CH_2)_2OH$, $-O(CH_2)_3OH$, $-(CH_2)_2OCH_3$ or $-O(CH_2)_2OCH_2CH_3$;

where R is hydroxy, amino, methylamino, ethylamino, dimethylamino, diethylamino, morpholino, piperidino, piperazino, N-methylpiperazino, $-NHCOR^6$, $-N(CH_3)COCH_3$, $-NHSO_2CH_3$, $-NHSO_2(CH_2)_3CH_3$, $-NR^5SO_2R^7$, $-NHSO_2NH_2$, $-NHSO_2N(CH_3)_2$, $-COOH$, $-COOCH_3$, $-COOCH_2CH_2CH_3$, $-CONH_2$, $-CON(CH_3)_2$, $-CON(CH_2CH_3)_2$, $-CON(CH_2CH_2CH_3)_2$,

$-SR^9$, $-SOCH_3$, $-SO_2CH_3$ or $-CN$;

$R^5$ represents a hydrogen atom or a methyl group;
$R^6$ is hydrogen or $C_{1-4}$ alkyl, $C_{1-4}$ alkoxy, phenyl, amino or N,N-dimethylamino;
$R^7$ represents phenyl;
$R^9$ is methyl, ethyl or phenyl; and
q is zero, 1, 2 or 3.

7. A compound according to claim 6 in which Ar is a phenyl group containing a single substituent which is $-CON(CH_2CH_3)_2$.

8. A compound of formula (Ia)

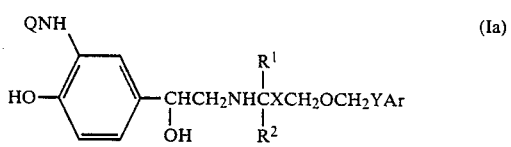

or a physiologically acceptable salt or solvate thereof wherein

X represents a $C_{1-7}$ alkylene, $C_{2-7}$ alkenylene or $C_{2-7}$ alkynylene chain;

Y represents a bond, or a $C_{1-6}$ alkylene, $C_{2-6}$ alkenylene or $C_{2-6}$ alkynylene chain with the proviso that the sum total of carbon atoms in the chains X and Y is 5, 6 or 7;

$R^1$ and $R^2$ each independently represent a hydrogen atom or a methyl group;

Q represents HCO—, $NH_2CO$—, $(CH_3)_2NSO_2$— or $CH_3SO_2$—; and

Ar represents a phenyl group substituted by a group selected from amino, dimethylamino, nitro, morpholino, $(CH_2)_qNHCOR^6$, $-NHSO_2R^7$, $-COR^8$, $-CH_2CONR^3R^4$, $-SR^9$ or $-(CH_2)_rR^{10}$;

where $R^6$ is $C_{1-4}$ alkyl and q is zero or 1, $R^7$ is $C_{1-4}$ alkyl, $R^8$ is $C_{1-4}$ alkoxy or $-NR^3R^4$ where $R^3$ and $R^4$ are both $C_{1-4}$ alkyl or $-NR^3R^4$ in the group $-CONR^3R^4$ may also form a piperidino ring, $R^9$ is $C_{1-4}$ alkyl, and $R^{10}$ is $C_{1-4}$ alkoxy and r is 3;

or Ar is 3,5-dihydroxyphenyl or 3-methoxy-4-hydroxyphenyl, or, when X and/or Y represent an alkenylene or alkynylene group, Ar may additionally repesent a phenyl group optionally substituted by a fluorine atom.

9. A compound according to claim 8 in which Q represents $CH_3SO_2$—.

10. A compound according to claim 8 in which Ar is a phenyl group containing a single substituent which is $-CON(CH_2CH_3)_2$.

11. N,N-Diethyl-4-[4-[[6-[[2-hydroxy-2-[4-hydroxy-3-[(methylsulphonyl)amino]phenyl]ethyl]amino]hexyl]oxy]butyl]benzamide or a physiologically acceptable salt or hydrate thereof.

12. A pharmaceutical composition for therapy or prophylaxis of a disease associated with reversible airways obstruction such as asthma or chronic bronchitis, which comprises an effective amount to alleviate or for prophylaxis of said disease of at least one of the compounds as defined in claim 11, together with physiologically acceptable carriers and excipients.

13. A pharmaceutical composition for the treatment of premature labor, depression, congestive heart failure, an inflammatory or allergic skin disease, glaucoma or a condition in which there is an advantage in lowering gastric acidity, such as gastric or peptic ulceration, which comprises an effective amount to alleviate said condition of at least one compound as defined in claim 11, together with a physiologically acceptable carrier or diluent.

14. A compound selected from:

N-[2-hydroxy-5-[1-hydroxy-2-[[6-[4-(3,5-dihydroxyphenyl)butoxy]hexyl]amino]ethyl]phenyl]methanesulphonamide;

N-[2-hydroxy-5-[1-hydroxy-2-[[6-[4-(4-hydroxy-3-methoxyphenyl)butoxy]hexyl]amino]ethyl]phenyl]methanesulphonamide;

N-[2-hydroxy-5-[1-hydroxy-2-[[6-[4-(4-(methylthio)-phenyl]butoxy]hexyl]amino]ethyl]phenyl]methanesulphonamide;

N-[2-hydroxy-5-[1-hydroxy-2-[[6-[4-(4-nitrophenyl)-butoxy]hexyl]amino]ethyl]phenyl]methanesulphonamide;

N-[5-[2-[[6-[4-(4-aminophenyl)butoxy]hexyl]amino-1-hydroxyethyl]-2-hydroxyphenyl]methanesulphonamide;

propyl 4-[4-[[5-[[2-hydroxy-2-[4-hydroxy-3-[(methylsulphonyl)amino]phenyl]ethyl]amino]pentyl]oxy]butyl]benzoate;

N-[[4-[4-[[6-[[2-hydroxy-2-[4-hydroxy-3-[(methylsulphonyl)amino]phenyl]ethyl]amino]hexyl]butyl]phenyl]methyl]pentanamide;

N-[2-hydroxy-5-[1-hydroxy-2-[[5-[4-[4-(3-methoxypropyl)phenyl]butoxy]pentyl]amino]ethyl]phenyl]formamide;

N-[4-[4-[[6-[[2-[3-[(aminocarbonyl)amino]-4-hydroxyphenyl]ethyl]amino]hexyl]oxy]butyl]phenyl]butanesulphonamide;

N-[2-hydroxy-5-[1-hydroxy-2-[[6-(4-phenylbutoxy)-3-hexynyl]amino]ethyl]phenyl]methanesulphonamide;

(E)-N-[2-hydroxy-5-[1-hydroxy-2-[[6-[[4-(4-fluorophenyl)-3-butenyl]oxy]hexyl]amino]ethyl]phenyl]methanesulphonamide;

and physiologically acceptable salts and hydrates thereof.

15. A pharmaceutical composition for therapy or prophylaxis of a disease associated with reversible airways obstruction such as asthma or chronic bronchitis, which comprises an effective amount to alleviate or for prophylaxis of said disease of at least one compound of general formula (I) as defined in claim 1 or a physiologically acceptable salt or solvate thereof, together with physiologically acceptable carrier or excipient.

16. A pharmaceutical composition for the treatment of premature labour, depression, congestive heart failure, an inflammatory or allergic skin disease, glaucoma or a condition in which there is an advantage in lowering gastric acidity such as gastric or peptic ulceration, which comprises an effective amount to alleviate said condition of at least one compound of general formula (I) as defined in claim 1 or a physiologically acceptable salt or solvate thereof, together with a physiologically acceptable carrier or diluent.

* * * * *